United States Patent
Li et al.

(10) Patent No.: US 12,196,675 B2
(45) Date of Patent: Jan. 14, 2025

(54) SENSITIVE AND ROBUST BIOSENSING USING PLASMONIC ENHANCEMENT OF FLUORESCENCE BY RAPID THERMAL ANNEALED SILVER NANOSTRUCTURES

(71) Applicant: University of South Florida, Tampa, FL (US)

(72) Inventors: Shuangming Li, Santa Clara, CA (US); Venkat R. Bhethanabotla, Tampa, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 405 days.

(21) Appl. No.: 17/365,818

(22) Filed: Jul. 1, 2021

(65) Prior Publication Data
US 2022/0003674 A1 Jan. 6, 2022

Related U.S. Application Data

(60) Provisional application No. 63/047,055, filed on Jul. 1, 2020.

(51) Int. Cl.
| | |
|---|---|
| *G01N 21/64* | (2006.01) |
| *B82Y 15/00* | (2011.01) |
| *G01N 21/552* | (2014.01) |
| *G01N 33/543* | (2006.01) |
| *G01N 33/553* | (2006.01) |

(52) U.S. Cl.
CPC ....... *G01N 21/554* (2013.01); *G01N 21/6408* (2013.01); *G01N 21/648* (2013.01); *G01N 33/54346* (2013.01); *G01N 33/54373* (2013.01); *B82Y 15/00* (2013.01); *G01N 33/553* (2013.01)

(58) Field of Classification Search
CPC ............. G01N 21/554; G01N 21/6408; G01N 21/648; G01N 33/54346; G01N 33/54373; G01N 33/553; B82Y 15/00
See application file for complete search history.

(56) References Cited

U.S. PATENT DOCUMENTS 9,164,034 B2 * 10/2015 Rubinstein ............. B82Y 15/00

OTHER PUBLICATIONS

Bauch, M., et al. (2014). Plasmon-Enhanced Fluorescence Biosensors: a Review. Plasmonics (Norwell, Mass.), 9, 781-799. doi: 10.1007/s11468-013-9660-5 (Year: 2014).*
Jeong, Sunho et al., "Low-temperature solution-processed metal oxide thin film transistors". "J. Mater. Chem. vol. 22, issue 4, p. 1243-1250. (2012). doi =10.1039/C1JM14452A", (Year: 2012).*
Accardo, Angelo et al. (2014) "Metal Structures as Advanced Materials in Nanotechnology", Handbook of Nanomaterials Properties Apr. 2014. DOI:10.1007/978-3-642-31107-9_42 (Year: 2014).*
Haoyan Wei et al., "From silver nanoparticles to thin films: Evolution of microstructure and electrical conduction on glass substrates" , Journal of Physics and Chemistry of Solids, vol. 70, Issue 2, (2009) https://doi.org/10.1016/j.jpcs.2008.11.012. (Year: 2009).*
Agnihotri et al., "Size-controlled silver nanoparticles synthesized over the range 5-100 nm using the same protocol and their antibacterial efficacy." Rsc Advances 4, No. 8 (2014): 3974-3983.
Alonzo-Medina et al., "Understanding the thermal annealing process on metallic thin films." In IOP Conference Series: Materials Science and Engineering, vol. 45, No. 1, p. 012013. IOP Publishing, 2013.
Anker et al., "Biosensing with plasmonic nanosensors." Nanoscience and Technology: A Collection of Reviews from Nature Journals (2010): 308-319.
Aslan et al., "Metal-enhanced fluorescence solution-based sensing platform." Journal of fluorescence 14, No. 6 (2004): 677-679.
Aslan et al., "Metal-enhanced fluorescence: an emerging tool in biotechnology." Current opinion in biotechnology 16, No. 1 (2005): 55-62.
Chen et al., "Atomic force bio-analytics of polymerization and aggregation of phycoerythrin-conjugated immunoglobulin G molecules." Molecular immunology 41, No. 12 (2004): 1247-1252.
Chowdhury et al., "Effect of Ag—Cu alloy nanoparticle composition on luminescence enhancement/quenching." The Journal of Physical Chemistry C 113, No. 30 (2009): 13016-13022.
Chowdhury et al., "Silver-copper alloy nanoparticles for metal enhanced luminescence." Applied Physics Letters 95, No. 13 (2009): 131115.
Droz et al., "Influence of surface and protein modification on immunoglobulin G adsorption observed by scanning force microscopy." Biophysical journal 67, No. 3 (1994): 1316-1323.
Dulkeith et al., "Fluorescence quenching of dye molecules near gold nanoparticles: radiative and nonradiative effects." Physical review letters 89, No. 20 (2002): 203002.
Dulkeith et al., "Gold nanoparticles quench fluorescence by phase induced radiative rate suppression." Nano letters 5, No. 4 (2005): 585-589.
Erickson, "Size and shape of protein molecules at the nanometer level determined by sedimentation, gel filtration, and electron microscopy." Biological procedures online 11, No. 1 (2009): 32-51.
Geddes et al., "Metal-enhanced fluorescence." Journal of fluorescence 12, No. 2 (2002): 121-129.
Geddes et al., "Metal-enhanced fluorescence (MEF) due to silver colloids on a planar surface: Potential applications of indocyanine green to in vivo imaging." The Journal of Physical Chemistry A 107, No. 18 (2003): 3443-3449.
Herminghaus et al., "Spinodal dewetting in liquid crystal and liquid metal films." Science 282, No. 5390 (1998): 916-919.
Howarter et al., "Optimization of silica silanization by 3-aminopropyltriethoxysilane." Langmuir 22, No. 26 (2006): 11142-11147.

(Continued)

*Primary Examiner* — Elizabeth C. Kemmerer
*Assistant Examiner* — McKenzie A Dunn
(74) *Attorney, Agent, or Firm* — Quarles & Brady LLP

(57) ABSTRACT

Chips and metallic nanostructure biosensors comprising a dielectric substrate and discontinuous and disordered metallic nanostructures of flat island shapes thereon are disclosed herein. Also disclosed are methods of making and using the same.

25 Claims, 22 Drawing Sheets
(6 of 22 Drawing Sheet(s) Filed in Color)

(56) References Cited

OTHER PUBLICATIONS

Hsu et al., "Transparent displays enabled by resonant nanoparticle scattering." Nature communications 5, No. 1 (2014): 1-6.
Hu et al., "Nanoscale pattern formation in Pt thin films due to ion-beam-induced dewetting." Applied Physics Letters 76, No. 22 (2000): 3215-3217.
Kim et al., "Formation, structure, and reactivity of amino-terminated organic films on silicon substrates." Journal of colloid and interface science 329, No. 1 (2009): 114-119.
Konkola, "Design and analysis of a scanning beam interference lithography system for patterning gratings with nanometer-level distortions." PhD diss., Massachusetts Institute of Technology, 2003.
Lakowicz et al., "Radiative decay engineering: 2. Effects of silver island films on fluorescence intensity, lifetimes, and resonance energy transfer." Analytical biochemistry 301, No. 2 (2002): 261-277.
Li et al., "Electrochemical growth of two-dimensional gold nanostructures on a thin polypyrrole film modified ITO electrode." The Journal of Physical Chemistry B 109, No. 50 (2005): 23787-23793.
Liu et al., "Metal-enhanced immunofluorescence assays for detection of carcinoembryonic antigen." In 2017 IEEE Sensors, pp. 1-3. IEEE, 2017.
Liu et al., "Integrating metal-enhanced fluorescence and surface acoustic waves for sensitive and rapid quantification of cancer biomarkers from real matrices." ACS sensors 3, No. 1 (2018): 222-229.
Liz-Marzán, "Nanometals: formation and color." Colloidal Synthesis of Plasmonic Nanometals (2004): 26-31.
Pompa et al., "Metal-enhanced fluorescence of colloidal nanocrystals with nanoscale control." Nature nanotechnology 1, No. 2 (2006): 126-130.
Resnick et al., "Step & flash imprint lithography." Materials Today 8, No. 2 (2005): 34-42.
Ruffino et al., "Controlled dewetting as fabrication and patterning strategy for metal nanostructures." physica status solidi (a) 212, No. 8 (2015): 1662-1684.
Seo, Jung-Hun, Jung Ho Park, Seong-Il Kim, Bang Ju Park, Zhenqiang Ma, Jinnil Choi, and Byeong-Kwon Ju. "Nanopatterning by laser interference lithography: applications to optical devices." Journal of nanoscience and nanotechnology 14, No. 2 (2014): 1521-1532.
Silverton et al., "Three-dimensional structure of an intact human immunoglobulin." Proceedings of the National Academy of Sciences 74, No. 11 (1977): 5140-5144.
Srolovitz et al., "The thermodynamics and kinetics of film agglomeration." Jom 47, No. 3 (1995): 31-36.
Thompson, "Solid-state dewetting of thin films." Annual Review of Materials Research 42 (2012): 399-434.
Toma et al., "Fabrication of broadband antireflective plasmonic gold nanocone arrays on flexible polymer films." Nano letters 13, No. 12 (2013): 6164-6169.
Vandenberg et al., "Structure of 3-aminopropyl triethoxy silane on silicon oxide." Journal of colloid and interface science 147, No. 1 (1991): 103-118.
Vo-Dinh. "Surface-enhanced Raman spectroscopy using metallic nanostructures." TrAC Trends in Analytical Chemistry 17, No. 8-9 (1998): 557-582.
Wang et al., "Preparation and characterization of poly (N-isopropylacrylamide) films on a modified glass surface via surface initiated redox polymerization." Materials Letters 59, No. 14-15 (2005): 1736-1740.
Yadavali et al., "Pulsed laser dewetting of Au films: Experiments and modeling of nanoscale behavior." Journal of Materials Research 28, No. 13 (2013): 1715-1723.
Yue et al., "Electron-beam lithography of gold nanostructures for surface-enhanced Raman scattering." Journal of Micromechanics and Microengineering 22, No. 12 (2012): 125007.
Zabila et al., "Direct laser interference patterning: theory and application." Acta Physica Polonica-Series A General Physics 115, No. 2 (2009): 591.
Zhang et al., "Superlenses to overcome the diffraction limit." Nature materials 7, No. 6 (2008): 435-441.
Zhang et al., "Wavelength dependence of metal-enhanced fluorescence." The Journal of Physical Chemistry C 113, No. 28 (2009): 12095-12100.
Zhang et al., "Photomediated synthesis of silver triangular bipyramids and prisms: the effect of pH and BSPP." Journal of the American Chemical Society 132, No. 35 (2010): 12502-12510.
Araújo, A., et al., "Influence of the Substrate on the Mophology of Self-Assembled Silver Nanoparticles by Rapid Thermal Annealing", The Journal of Physical Chemistry C 2016 120 (32), 18235-18242 DOI: 10.1021/acs.jpcc.6b04283.
Lin, H., et al. (2017) A Large-Area Nanoplasmonic Sensor Fabricated by Rapid Thermal Annealing Treatment for Label-Free and Multi-Point Immunoglobulin Sensing. Nanomaterials, 7(5), 100. doi: 10.3390/nano7050100. pp. 1-11.
Tran, N., et al. (2018). Fluorescence Enhancement Using Bimetal Surface Plasmon-Coupled Emission from 5-Carboxyfluorescein (FAM). Micromachines, 9(9), 460. doi:10.3390/mi9090460. pp. 1-6.
Bauch, M., et al. (2014). Plasmon-Enhanced Fluorescence Biosensors: a Review. Plasmonics (Norwell, Mass.), 9, 781-799. doi:10.1007/s11468-013-9660-5.
Feng, T., et al. (2019). Deposition of gold nanoparticles upon bare and indium tin oxide film coated glass based on annealing process. Journal of Experimental Nanoscience, 14(1), 13-22. doi: 10.1080/17458080.2018.1520399.
Li, S., & Bhethanabotla, V. R. (2021). Sensitive biosensing using plasmonic enhancement of fluorescence by rapid thermal annealed silver nanostructures. IEEE Sensors Journal, 21(14), 15917-15925.

\* cited by examiner

SENSITIVE AND ROBUST BIOSENSING USING PLASMONIC ENHANCEMENT OF FLUORESCENCE BY RAPID THERMAL ANNEALED SILVER NANOSTRUCTURES

CROSS-REFERENCE TO RELATED APPLICATIONS

The present application claims priority to U.S. Provisional Patent Application No. 63/047,055 that was filed Jul. 1, 2021, the entire contents of which are hereby incorporated by reference.

STATEMENT REGARDING FEDERALLY SPONSORED RESEARCH

This invention was made with government support under 1640668 awarded by National Science Foundation. The government has certain rights in the invention.

BACKGROUND OF THE INVENTION

Although immunofluorescence assay has been used for decades, it is not capable of quantifying biomarkers at ng/ml levels. Plasmonic enhancement of fluorescence using metallic surface nanostructures has been shown to have potential in amplifying the fluorescence signal, which could enable low limits of detection with high sensitivity. However, current methods for fabricating metallic nanostructures, such as electron beam (E-beam) nanolithography, colloidal lithography, and colloidal self-assembly, require complicated processes and have various drawbacks.

SUMMARY OF THE INVENTION

In accordance with the present disclosure, a metallic nanostructure biosensor may be prepared from a chip comprising a dielectric substrate and discontinuous and disordered metallic nanostructures of flat island shapes thereon. Because the technology disclosed allows for fabrication over large areas, wafers comprising a multiplicity of chips may be prepared. This allows for the simultaneous preparation of a multiplicity of chips that may be separated after fabrication.

As demonstrated in the examples that follow, the morphology of the discontinuous and disordered metallic nanostructures may be controlled during fabrication of the chip. In some embodiments, the discontinuous and disordered metallic nanostructures of flat island shapes thereon are characterized in shape as hemi-spherical nanostructures. In some embodiments, the discontinuous and disordered metallic nanostructures of flat island shapes thereon are characterized in shape as ellipsoidal nanostructures or peanut-shaped nanostructures. In some embodiments, the discontinuous and disordered metallic nanostructures of flat island shapes thereon are characterized in shape as worm-like nanostructure or lace-like nanostructures. In some embodiments, the chip may comprise any combination of the foregoing discontinuous and disordered metallic nanostructures.

As demonstrated in the examples that follow, the discontinuous and disordered metallic nanostructures may be prepared with different metals. The metal used to prepare the nanostructures should be selected to enhance signal intensity or allow for MEF. In some embodiments, the nanostructures allow for an enhancement factor of about 1.1-20.0. In some embodiments, the nanostructures allow for an enhancement factor of about 1.1-5.0, 5.0-10.0, 10.0-15.0, or about 15.0-20.0. The discontinuous and disordered metallic nanostructures may comprise silver but other materials may be used provided that they enhance signal intensity or allow for MEF. Other examples of materials for use in the present technology include, without limitation, aluminum, gold, copper, or bimetallic materials. Bimetallic materials may include one or more of the foregoing but need not.

As demonstrated in the examples that follow, the surface coverage of the discontinuous and disordered metallic nanostructures may be controlled during fabrication of the chip. In some embodiments, the discontinuous and disordered metallic nanostructures cover about 20-40%, 23-37%, or 26-34% of the dielectric substrate.

As demonstrated in the examples that follow, the density of the discontinuous and disordered metallic nanostructures may be controlled during fabrication of the chip. In some embodiments, the discontinuous and disordered metallic nanostructures have a density of about 5-600/$\mu m^2$. In some embodiments, the discontinuous and disordered metallic nanostructures have a density of about 5-100/$\mu m^2$, 100-200/$\mu m^2$, 200-300/$\mu m^2$, 300-400/$\mu m^2$, 400-500/$\mu m^2$, or 500-600/$\mu m^2$. In some embodiments, the discontinuous and disordered metallic nanostructures have a density of about 5-30/$\mu m^2$, 5-20/$\mu m^2$, or 5-10/$\mu m^2$. In some embodiments, the discontinuous and disordered metallic nanostructures have a density of about 30-100/$\mu m^2$, 40-90/$\mu m^2$, 50-80/$\mu m^2$, or 60-70/$\mu m^2$.

As demonstrated in the examples that follow, the average height of the discontinuous and disordered metallic nanostructures may be controlled during fabrication of the chip. In some embodiments, the discontinuous and disordered metallic nanostructures have an average height of about 10-60 nm as calculated by eqn. 4. In some embodiments, the discontinuous and disordered metallic nanostructures have and average height about 10-15 nm, 15-20 nm, 20-25 nm, 25-30 nm, 35-40 nm, 40-45 nm, 45-50 nm, or 55-60 nm. In some embodiments, the discontinuous and disordered metallic nanostructures have and average height about 35-60, 40-55 nm, or 45-50 nm. In some embodiments, the discontinuous and disordered metallic nanostructures have and average height about 15-45, 20-40 nm, or 25-35 nm.

As demonstrated in the examples that follow, the area of the discontinuous and disordered metallic nanostructures may be controlled during fabrication of the chip. In some embodiments, the discontinuous and disordered metallic nanostructures have an area of about 50-250,000 nm. In some embodiments, the discontinuous and disordered metallic nanostructures have an area of about 50-2,500 nm. In some embodiments, the discontinuous and disordered metallic nanostructures have an area of about 200-15,000 nm. In some embodiments, the discontinuous and disordered metallic nanostructures have an area of about 5,000-250,000 nm.

In some embodiments, the chip comprises a stabilizing overlayer. The stabilizing overlayer stabilizes the nanostructures on the dielectric substrate. As demonstrated in the examples, the material used to prepare the nanostructures may be selected to enhance signal intensity or improve MEF. In some embodiments, the stabilizing overlayer allows for a signal enhancement factor of more than 2.0, 2.5, 3.0, 3.5, 4.0, 4.5, 5.0, 5.5, 6.0, or 6.5 as compared to a chip without a stabilizing overlayer. In some embodiments, the stabilizing overlayer allows for a signal enhancement factor of about 2.0-7.0. In some embodiments, the stabilizing overlayer allows for a signal enhancement factor of about 2.0-3.0, 3.0-4.0, 4.0-5.0, 5.0-6.0, or 6.0-7.0. In some embodiments, the stabilizing overlayer comprises a metal oxide, such as SiO$_2$ or AnO) or a polymer, such as polymethyl methacrylate (PMMA), but other materials may be used.

As demonstrated in the examples, the selection of the thickness of the stabilizing overlayer allows for a signal enhancement. In some embodiments, the stabilizing overlayer is a thin film. Suitably, the thin film of stabilizing overlayer may be between about 2-15 nm thick. In some embodiments, the stabilizing overlayer is about 2-8 nm, 3-9 nm, 4-10 nm, 6-12 nm, or about 7-13 nm thick.

In some cases, the stabilizing overlayer can protect the nanostructures from oxidizing during storage or operation.

The dielectric substrate selected should allow for RTA and preparation of the chips or wafers described herein. The spreading coefficient S may be used to select a dielectric substrate suitable for use with a metallic film. In some embodiments, the dielectric substrate is a glass substrate, such as SiO$_2$, but other materials may be used. In some embodiments, the dielectric substrate comprises a piezoelectric material. Exemplary materials for use in the dielectric substrate include, without limitation, liNbO$_3$, quartz, LiTaO$_3$.

Another aspect of the invention provides for a metallic nanostructure biosensor. The metallic nanostructure biosensor comprises any of the chips described herein and a target binding protein immobilized onto the chip. A target binding protein refers to a protein, a fragment thereof, or a polypeptide capable of binding a biomolecular target. The target binding protein may be immobilized to the chip via a molecular tether. Molecular tethers are capable of forming a covalent or non-covalent linkage between to the target binding protein and the chip. In some embodiments, the molecular tether is a silane, such as APTES, but other molecular tethers may be utilized.

A biomolecular target refers to a compound or substance from a biological source where the qualitative presence or absence or quantitative amount of which is desired to be known. In some embodiments, the biomolecular target is a protein, such as an antibody, or a carbohydrate, such as chitin. Suitably the target binding protein has binding affinity for the biomolecular target. In some embodiments, the binding affinity is selective.

In some embodiments, the target binding protein may be a fragment crystallisable (Fc) binding protein, such as Protein A. When the target binding protein is an Fc binding protein, the biomolecular target may be an antibody. This allows for binding of the target antibody while leaving the target antibody's antigen-binding site free for binding an antigen or anti-antibody.

In some embodiments, the target binding protein may be a carbohydrate binding protein, such as a lectin. When the target binding protein is a carbohydrate binding protein, the biomolecular target may be a carbohydrate such as a chitin or surface-bound chitin on a cell or other vesicle. For example, chitin may comprise a portion of a cell wall of a fungus.

In some embodiments, the metallic nanostructure biosensor further comprises a target probe. A target probe refers to substance or compound capable of providing a detectable signal, such as a fluorescence signal. The target probe should be capable of interacting with the biomolecular target such that a signal obtained from the target probe provides qualitative or quantitative information about the presence, absence, or amount of the biomolecular target. In some embodiments, the target probe is selective for the biomolecular target. In embodiments where the biomolecular target is an antibody, the target probe may be a labeled anti-antibody or labeled antigen capable binding the target antibody's antigen binding site.

In some embodiments, metallic nanostructure biosensor comprises a blocking agent. A blocking agent refers to a substance capable of inhibiting non-specific binding of the bimolecular target or other components of a sample with the metallic nanostructure biosensor. In some embodiments, the blocking agent is an albumin, such as BSA, but other blocking agents may be utilized.

Another aspect of the invention is a method for fabricating any of the chips described herein or a wafer comprising a multiplicity of the chips. The method may comprise depositing a thin metallic film on a dielectric substrate and applying rapid thermal annealing to the metallic film to produce the discontinuous and disordered metallic nanostructures of flat island shapes. In some embodiments, the metallic film is less than 25 nm thick. In some embodiments, the metallic film is about 2-8 nm, 4-10 nm, 6-12 nm, 8-14 nm, 10-16 nm, 12-18 nm, 14-20 nm, or 16-22 nm. As demonstrated by the examples, controlling the thickness of the metallic film allow for controlling the morphology, surface coverage, area density, average height, area of the metallic nanostructure, or any combination thereof. The metallic thin film may be applied by sputtering or electron beam deposition, but other methods for applying the thin film may also be utilized.

In some embodiments, the rapid thermal annealing occurs at a temperature lower than a melting point of the metallic film. As demonstrated in the examples, the presently disclosed where prepared by annealing a thin metallic film of silver at 500° C., which has a melting point of 961.8° C. In some embodiments, rapid thermal annealing occurs at a temperature less than about 90%, 85%, 80%, 75%, 70%, 65%, 60%, or 55% of the melting point of the metal present in the metallic film.

Rapid thermal annealing may comprise heating the thin metallic film and the dielectric substrate up to an annealing temperate at an annealing rate, holding the thin metallic film and the dielectric substrate at the annealing temperature of an annealing time, and cooling the thin metallic film and the dielectric substrate to room temperature at a cooling rate. For example, the thin metallic film and dielectric substrate may be heated to an annealing temperature of 500° C. at a annealing rate of 25° C./s, holding the thin metallic film and dielectric substrate at the annealing temperature for an annealing time of 60 s, then gradually cooling the thin metallic film and dielectric substrate to room temperature but other annealing temperatures, annealing rates, annealing time, and cooling rates may be utilized. In some embodiments, the annealing temperature may be between about 400° C.-800° C. In some embodiments, the anneal rate is from about 15° C./s-50° C. In some embodiments, the holding time is from about 30 secs to 2 mins. In some embodiments, the cooling rate may be about 5° C.-10° C./min In some embodiments, the method further comprises coating the discontinuous and disordered metallic nanostructures of flat island shape with a thin stabilizing overlayer film.

Another aspect of the invention provides for methods for forming a metallic nanostructure biosensor. The method may comprise immobilizing a target binding protein on any of the chips described herein. In some embodiments where the chip comprises the stabilizing overlayer, the target binding protein is immobilized onto the stabilizing overlayer.

Another aspect of the invention provides for detecting a biomolecular target in a sample The method may comprise contacting any of the metallic nanostructure biosensors described herein with the sample and a target probe, irradiating the metallic nanostructure biosensor, and detecting a signal, wherein the biomolecular target has binding affinity with the immobilized binding protein and the target probe. Contacting the metallic nanostructure biosensors with the sample refers to positioning the sample into proximity with the metallic nanostructure biosensor such that a biomolecular target, if present in the sample, is capable of binding with a target binding protein. Contacting the metallic nanostructure biosensors with the target probe refers to positioning the target probe into proximity with the metallic nanostructure biosensor such that a biomolecular target, if present in the sample, is capable of binding with the biomolecular target bound to a target binding protein. When a target binding protein, biomolecular target, and target probe form a tertiary complex in proximity to the chip, detectable signal intensity may be enhanced. This allows for a low limit of detection. Low limit of detection refers to a limit of detection less than about 100 ng/ml, less than about 50 ng/ml, 20 ng/ml, 10 ng/ml, 5 ng/ml, 2 ng/ml, or less than 1 ng/ml.

In some embodiments, the sample may originate from a subject. Suitably, the sample may comprise a biofluid collected therefrom. For example, the sample may comprise, without limitation, saliva, blood, serum, urine, cerebrospinal fluid, interstitial fluid, and other fluid samples. In some embodiments, the sample may be used as obtained from the subject. In other embodiments, the sample is processed to make detection of the biomolecular target more amenable.

Subject or patient refers to mammals and non-mammals. A mammal may be any member of the class Mammalia including, but not limited to, humans, non-human primates (e.g., chimpanzees, other apes, and monkey species), farm animals (e.g., cattle, horses, sheep, goats, and swine), domestic animals (e.g., rabbits, dogs, and cats), or laboratory animals including rodents (e.g., rats, mice, and guinea pigs). Examples of non-mammals include, but are not limited to, birds, and the like. The term subject does not denote a particular age or sex. In one specific embodiment, a subject is a mammal, preferably a human. The subject may have or suffer from, or be suspected of having or suffering from, a disease, condition, or disorder, such as cancer. The presence, absence, or quantitative amount of the biomolecular target may be useful for diagnosing or monitoring the disease, condition, or disorder or for providing prognosis regarding the disease, condition, or disorder.

These and other aspects of the invention will be further described herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention.

(FIG. 8A) 5 nm; (FIG. 8B) 10 nm; (FIG. 8C) 15 nm; and (FIG. 8D) 25 nm in accordance with the present disclosure.

(FIG. 10A) 5 nm; (FIG. 10B) 10 nm; (FIG. 10C) 15 nm; and (FIG. 10D) 25 nm, in accordance with the present disclosure.

(FIG. 14B) 10 nm Ag @ 5 nm $SiO_2$; (FIG. 14C) 10 nm Ag @ 10 nm $SiO_2$; (FIG. 14D) 15 nm Ag @ 5 nm $SiO_2$; and (FIG. 14E) 15 nm Ag @ 10 nm $SiO_2$, in accordance with the present disclosure.

DETAILED DESCRIPTION OF THE INVENTION

Figure 1A:
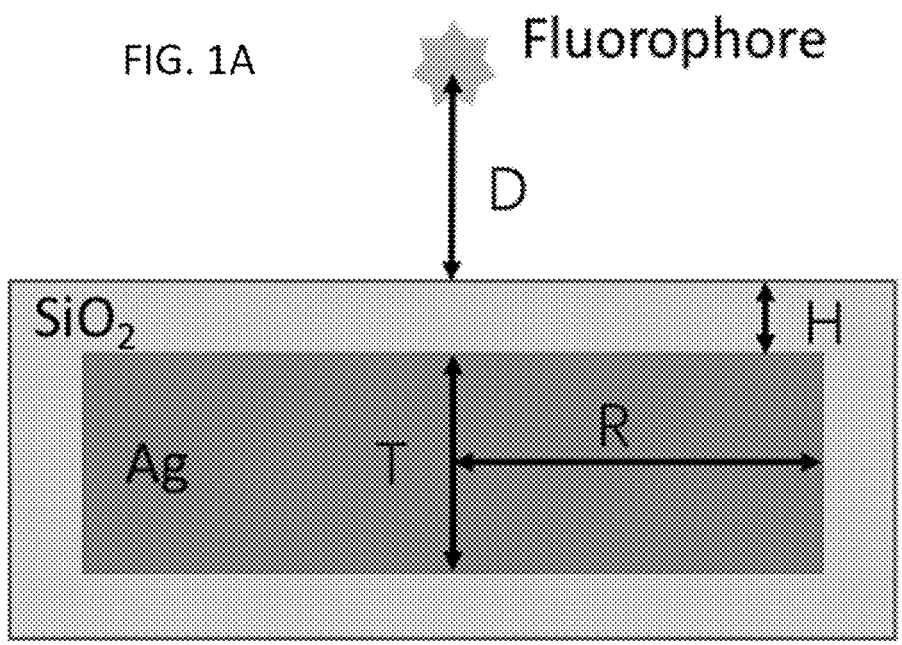
FIG. 1A shows a schematic of a finite difference time-domain (FDTD) computational model of an exemplary rapid thermal annealing (RTA) treated metallic nanostructure in accordance with various embodiments of the present disclosure.

The present disclosure describes various embodiments of systems, apparatuses, and methods of fabricating rapid thermal annealing (RTA) treated metallic nanostructures on a substrate. As such, the present disclosure describes an exemplary technique using straightforward processing steps for repeatable and scalable production of plasmonic structures that enhance sensor signals in immunofluorosensing applications, such as in cancer biomarker detection. Currently, without such enhancement, immunofluorosensing is incapable of detecting at low concentrations at which these biomarkers are present in body fluids. The described technology contributes to the design and manufacture of point of care diagnostic devices for biomarker detection and should be of interest to those developing sensing platforms for such detection.

Florescence has been applied for sensing technology in many areas such as protein, DNA, and cell detection[1]. Metallic surfaces can affect fluorescence in various ways—quench, increase rates of excitation, and/or increase quantum yields[2]. Silver and gold nanostructures generating surface plasmon resonance in the visible range of wavelength have been widely used in biosensing[3], surface enhanced Raman spectroscopy[4], near-field optics[5], etc.

Nano-scale metallic particles or structures can alter the fluorophores' free-space condition and can result in dramatic spectral changes. Metal surfaces can increase or decrease the radiative decay rates of fluorophores and can increase the extent of resonance energy transfer. These effects of metallic surfaces include three mechanisms: energy transfer quenching at short distances (~0-5 nm), concentration of the incident light field (~0-15 nm), and increasing the intrinsic radiative decay rate of the fluorophore (~0-20 nm)[6]. The use of fluorophore-metal interactions in biotechnology has primarily been referred to as radiative decay engineering or metal-enhanced fluorescence (MEF)[7]. The free-space quantum yields ($Q_o$) and the enhanced fluorescence signal's quantum yield ($Q_m$) of fluorophores in close proximity to metallic nanostructures can be described by the following equations[8]:

$$Q_o=\Gamma/(\Gamma+k_{nr}) \quad (1)$$

$$Q_m=(\Gamma+\Gamma_m)/(\Gamma+\Gamma_m+k_{nr}) \quad (2)$$

where $\Gamma$ is the unmodified radiative decay rate and $k_{nr}$ is the non-radiative rate. The presence of a nearby metallic surface increases the radiative rate by the addition of a new rate $\Gamma_m$.

Several prior methods to realize the metal-enhanced fluorescence effect on substrates have been reported in the literature. Generally, methods for fabricating nanopatterns on a substrate are not practical, and are unsuitable for large areas required in biosensing applications. Electron beam (E-beam) lithography is a widely used method to establish nanostructures[9]. Electron beam lithography involves resorting to metal lift-off or plasma etching. Electron beam lithography provides high resolution and reproducibility, with precise pattern control over the geometry down to the nanometer scale. However, in addition to requiring expensive equipment, electron beam lithography is impractical for large area fabrication.

Another prior method is photo or laser-interference lithography[10-11]. Laser-interference lithography exposes a photoresist layer with two or more coherent light beams, providing a nanolithography technique for periodically patterned structures. Laser-interference lithography method requires a specially designed optical system with beam splitters and mirrors to generate multiple light beams. The angles of incidence can be varied by changing the distances between mirrors or between a sample plane and a mirror plane. When the beams reach the sample surface, optical interference occurs, resulting in various interference patterns. Although providing a rapid and larger-area nanolithography process, laser-interference lithography still requires a complicated optical system and a precise alignment platform[12].

Nanoimprint lithography is another method for fabricating nanometer scale patterns on a large scale[13]. A mold is first fabricated using conventional electron beam lithography. The mold patterns are transferred to the photoresist layer on the sample substrate via ultraviolet (UV) and imprint processes. However, this method typically requires fabrication of a precise nanopattern mold, a release layer, and a special imprinting system.

Some self-masked methods such as polystyrene beads[14] or colloidal lithography's are also reported. These methods use small particles such as polystyrene beads or metal particle coatings on the substrate. Coating patterns with the area covered and uncovered work as masks for lithography process, such as metal deposition and dry etching. Such methods require no complicated lithography process requiring large fabrication times. However, the pattern quality and shape are highly dependent on the assembly area density and space between each particle.

There are also some methods not using lithography, such as electrochemical growth[16] or nanoparticle assembly[7,17]. Using colloid chemistry, metal nanoparticles with various structures such as triangular prisms, cubes, rods, and wires can be synthesized[18]. These allow for investigation of the effect of nanoparticle size, composition, and self-assembly; however, uniform distribution of these particles on the surface is a problem, as is assuring their stability during sensor usage.

In previous publications[19-20], we have reported on the effect of nanoparticle structure and compositions on metal-enhanced fluorescence (MEF). In a recent publication[21], we have utilized MEF from colloidally synthesized silver nanocubes dispersed on a substrate to construct a biosensor for the cancer marker carcinoembryonic antigen (CEA) to demonstrate quantification in the low ng/ml levels. The quantum yield enhancement is dependent on the nanocube dimension, areal density, and distance between fluorophores and the particle surface. Although successful at lowering the detection limit and allowing for detection in a surface acoustic wave sensor platform, the silver nanocubes based MEF immunofluorescence assay has several drawbacks. Notable among them are the unreliable colloidal synthesis procedure and its scale-up, difficult to achieve uniform distribution of the nanocubes on the surface at specified areal density, and difficulty with adhesion of these cubes to the surface through the sensing process. The colloidal synthesis and assembly of nanoparticles is sensitively influenced by many factor, such as reaction time, temperature control, and surface modification. The adhesion of particles to a sensor surface while retaining MEF and without affecting sensor performance is not easily achieved. Both of these factors preclude the use of nanoparticles produced by colloidal synthesis in MEF-based biosensor applications.

To overcome these issues, and obtain easier and faster nanostructure fabrication, the present disclosure utilizes a rapid thermal annealing (RTA) process to obtain stable nanostructures, in accordance with various embodiments. Upon optimization and after coating with a stabilizing overlayer, a stable nanostructure is able to be achieved that shows exceptionally large MEF, allowing for the construction of a robust, sensitive, and a low limit of detection (LOD) biosensor suitable for cancer biomarker quantification.

RTA is typically utilized for intrinsic stress liberation, improving structures, and controlling surface roughness in materials[22]. Metallic thin films deposited on dielectric substrates are typically thermodynamically unstable or substable. The spreading coefficient S determines if the liquid spontaneously spreads (S>0) or coagulates (S<0), with S defined as[23]:

$$S = \gamma_{sg} - \gamma_{lg} - \gamma_{ls} \quad (3)$$

The interfacial tensions of solid-gas ($\gamma_{sg}$), liquid-gas ($\gamma_{lg}$), and liquid-solid ($\gamma_{ls}$) interfaces, represent the surface energy between each of these interface. Spontaneous dewetting of metallic thin films on a dielectric substrate to form nanoparticles has been studied, and can be achieved via thermal[24], laser treatment[25-26], ion bombardment[27], etc. The complex mechanisms involved in forming the nanostructures have been investigated via molecular dynamics and continuum approaches; however, the different length and time scales involved make it difficult to predict the nonlinear dewetting dynamics to quantitatively assess film thickness dependent nanostructure characteristics[28]. An important weakness in realizing nanostructures via spontaneous dewetting of thin films is difficulty in process modeling and control, leading to nonuniformity in particle size and structure, and to defects. Fortunately, MEF is largely tolerant to such imperfections.

In accordance with various embodiments, RTA can be utilized to perturb the film into discontinuous droplets of flat island shapes, to reach a new, equilibrium structure that minimizes the interfacial energy. When the metallic film is very thin, this process can occur at a temperature much lower than its melting point. After the RTA process, disordered nano-islands are formed, allowing for the fabrication of large-area nanostructures on the substrate. The value of such micron-sized island structures, which exhibit nano-size in only the direction perpendicular to the substrate, in plasmonically enhancing fluorescence from fluorophore-conjugated antibodies in immunosensing is noted and is a focus of the present disclosure. In addition, the RTA treated nano-islands are observed to not be strongly attached to the substrate. Hence, in various embodiments, the RTA treated nano-islands are coated with a thin stabilizing overlayer to not only help stabilize the nanostructures, but also to protect the silver from oxidizing during sensor storage and operation.

Figure 1B:
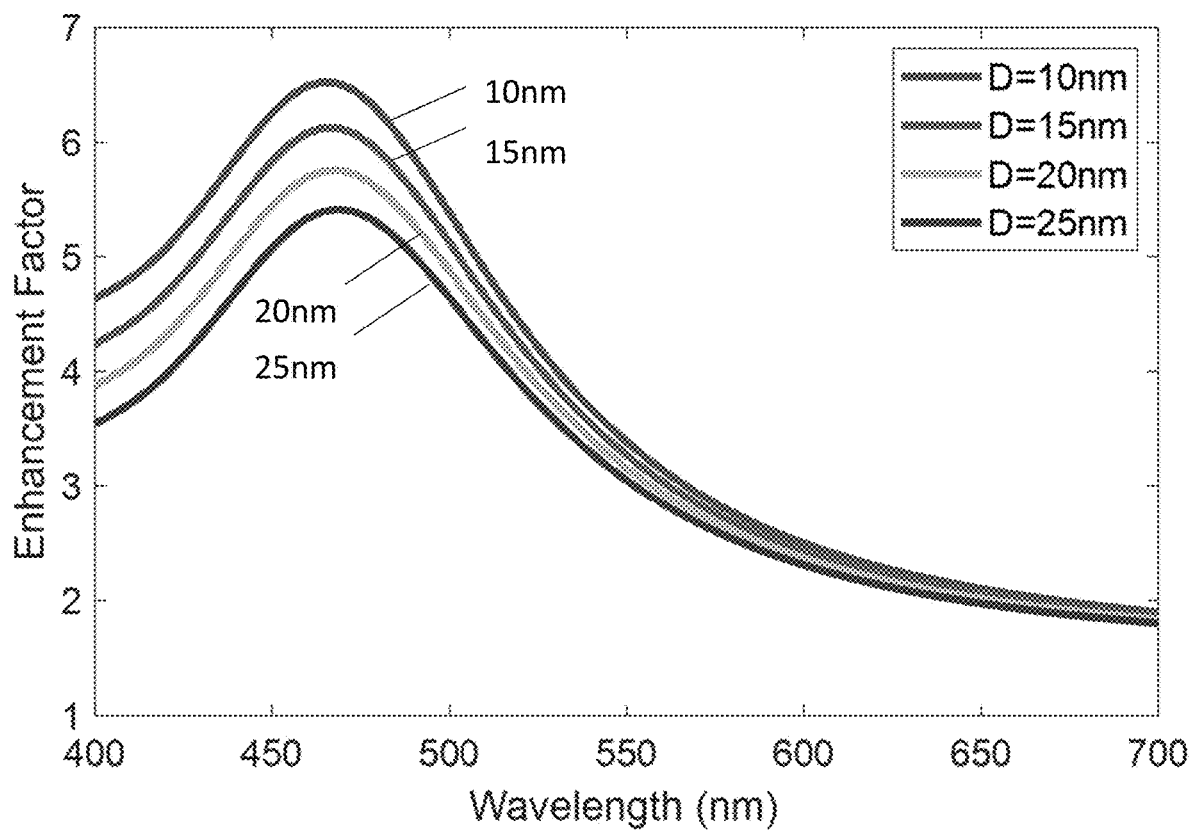
FIG. 1B shows a computed fluorescence enhancement factor as a function of distance between the fluorophore and silver particle surface of the RTA treated metallic nanostructure of FIG. 1A.

Finite difference time-domain (FDTD) simulation is widely used in computational electrodynamics. FDTD simulations are utilized in the present disclosure to predict fluorescence enhancement for a model system suitable to help with the device design. FIG. 1A shows a schematic of an exemplary FDTD computational model, in which a fluorophore is localized above the nanoparticle; the annealed silver particle is idealized as a circular disk, of radius (R), thickness (T) and silica coating layer height (H); and the fluorophore is considered to be a dipole located at a distance D from the particle surface. FIG. 1B shows a computed fluorescence enhancement factor as a function of distance between the fluorophore and silver particle surface. In this simulation, T=50 nm, R=200 nm, H=0 nm, and D=10 to 25 nm. FIG. 1B demonstrates that the enhancement factor is depended on the distance between the particle surface and the fluorophore.

Figure 2:
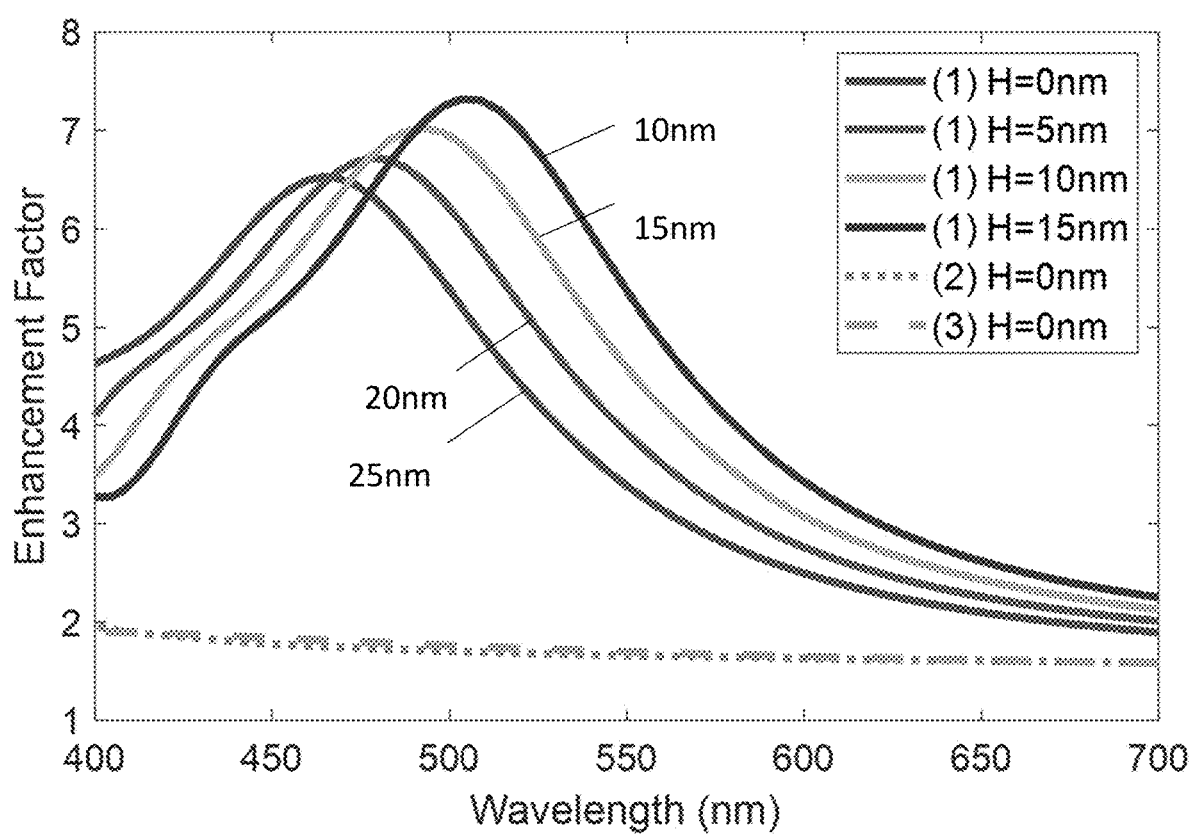
FIG. 2 shows a graph of computed fluorescence enhancement factor for several $SiO_2$ coating thicknesses in accordance with various embodiments of the present disclosure.

For the FDTD simulations, calculations were performed for nanoparticles without silica coating (H=0 nm) for particles of thickness T equal to 50 nm, 25 nm, and 15 nm. The particle radius R selected for each thickness was based on the experimental size distribution results, with average particle diameter being 200 nm, 50 nm, and 20 nm, respectively. FIG. 2 shows a computed fluorescence enhancement factor for several $SiO_2$ coating thicknesses in accordance with various embodiments of the present disclosure. In these simulations, (1) solid lines are for: T=50 nm, R=200 nm, D=10 nm, H=0 nm to 15 nm; (2) dotted line is for: T=15 nm, R=20 nm, D=10 nm, H=0 nm; and (3) dashed line is for: T=25 nm, R=50 nm, D=10 nm, H=0 nm.

FIG. 2 shows that the thickest nanoparticle (T=50 nm) enhances florescence the most, compared to the other two cases, whose enhancement factors are less than 2. The silica coating layer also has an effect on the spectrum. Increasing silica thickness (H) red shifts the spectrum peak from 464 nm to 503 nm. For the typical fluorophore, such as Alexa 488, the emission peak is at 520 nm, for which the 15 nm silica layer shows an enhancement factor to 7.01 compared to 4.42 for silica thickness of 0 nm. These simulations provide guidance to selecting optimal nanoparticle sizes and silica layer thickness to achieve maximum enhancement for a given fluorescence dye.

For experimental analysis, all materials and reagents were of analytical grade and were used as received. Rabbit immunoglobulin (IgG), bull serum albumin (BSA), and (3-aminopropyl)-triethoxysilane (APTES) were purchased from Sigma-Aldrich. Mouse anti-rabbit IgG-CFL 488 was purchased from Santa Cruz Biotechnology. Protein A was purchased from Abcam. Reagent grade deionized water (DI water) with 18.2 MΩ-cm resistivity was produced in the laboratory using a Millipore system. The instruments utilized in the experiments were a Hitachi SU-70 Scanning Electron Microscope (SEM); a Nikon FN1 fluorescence microscope; an MTI rapid thermal processor; and a Jasco V-670 spectrophotometer.

Figure 3:
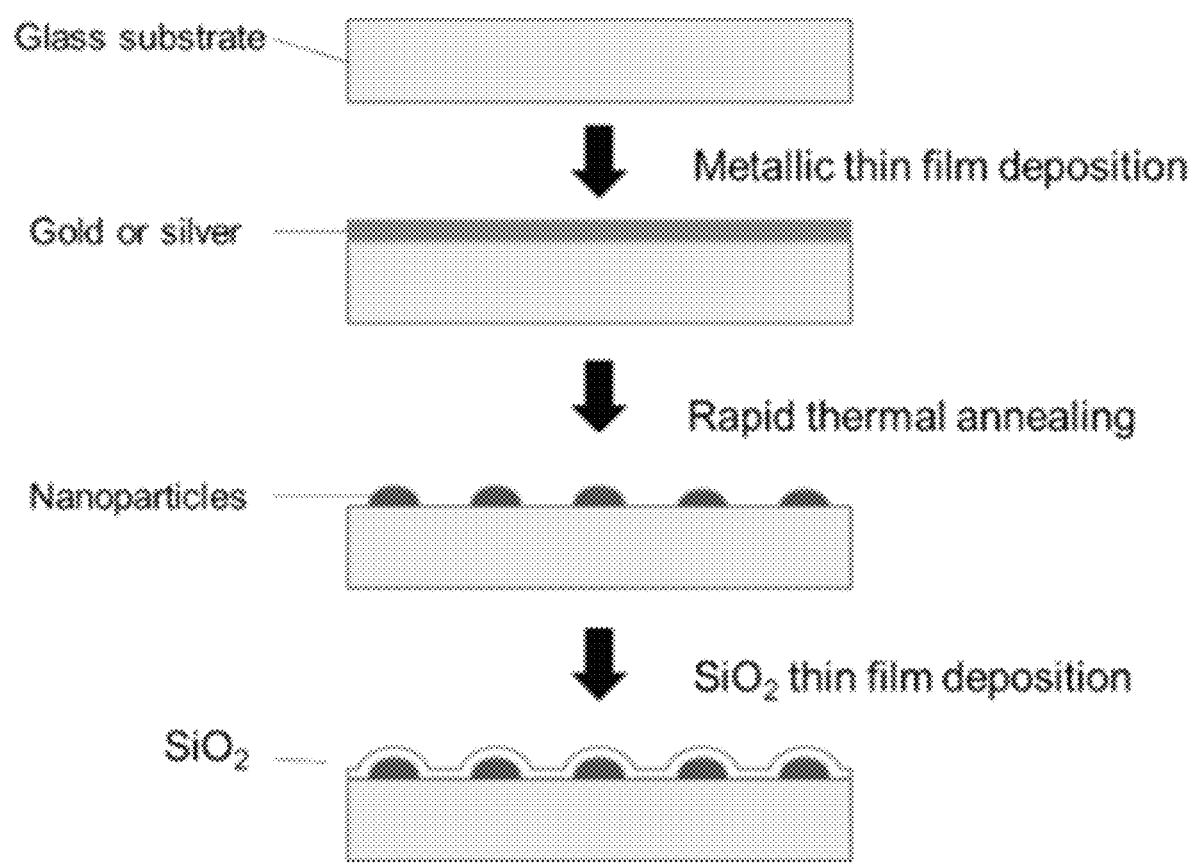
FIG. 3 is a schematic illustration of an exemplary fabrication process for RTA treated metallic nanostructures with silica coating layer on a glass substrate in accordance with various embodiments of the present disclosure.

FIG. 3 illustrates an exemplary chip fabrication process in accordance with various embodiments of the present disclosure. Glass slides were cleaned using a piranha solution (concentrated sulfuric acid: 30% hydrogen peroxide solution in ratio of 3:1). After solvent cleaning, a thin metal (gold or silver) film was deposited on the slides. E-beam evaporation and sputtering were both used to evaluate the deposition quality. The deposition rate was set to no faster than 2.5 Å/s for obtaining a homogeneous film. In one optimized process, the slides were treated by the rapid thermal annealing (RTA) process in which the slides were rapidly heated up to 500° C. at a rate of 25° C./s and held for 60 seconds. Then, the slides were cooled down to room temperature gradually. The entire process was conducted in a $N_2$ gas atmosphere in an MTI rapid thermal processor. The nanostructured patterns were generated after this annealing treatment. A thin $SiO_2$ layer was sputtered on the annealed slide surface with a deposition rate of 4 Å/min. The fabricated slides may be diced into individual chips.

Figure 4A:
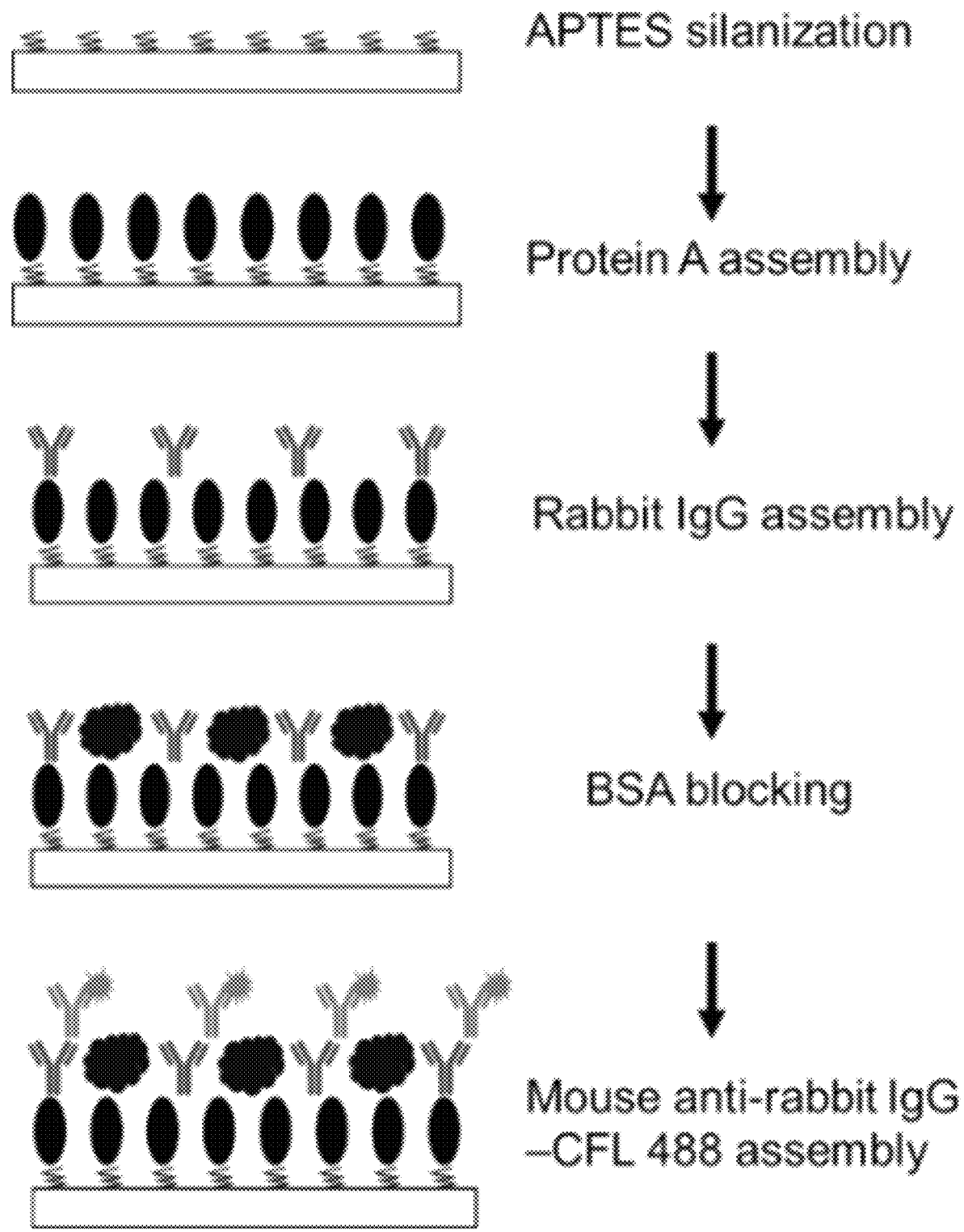
FIG. 4A is a schematic diagram of an exemplary chip modification process for fluorescence immunoassays in accordance with various embodiments of the present disclosure.

FIG. 4A is a schematic diagram of an exemplary chip modification process for fluorescence immunoassays in accordance with various embodiments of the present disclosure. The fabricated slides were solvent rinsed, dried with $N_2$ gas, and ten mM APTES in pure ethyl alcohol solution was used to silane treat the slide surface. After 1 hour of soaking, the chips were washed with pure ethyl alcohol and dried with $N_2$ gas. Protein A of 200 µg/ml in PBS (Phosphate-Buffered Saline) solution was first incubated for 2 hours at room temperature. Rabbit IgG was assembled for 2 hours, followed by 1 mg/ml BSA in PBS solution for blocking the unbound sites on the substrate. Then, 4 µg/ml mouse anti rabbit IgG-CFL 488 as the detection antibody was applied for fluorescence tests. The IgG conjugate Cruz Fluor™ 488 has an excitation peak of 491 nm, and an emission peak of 520 nm. The chips were rinsed with PBS solution and dried with $N_2$ gas between each step.

Figure 4B:
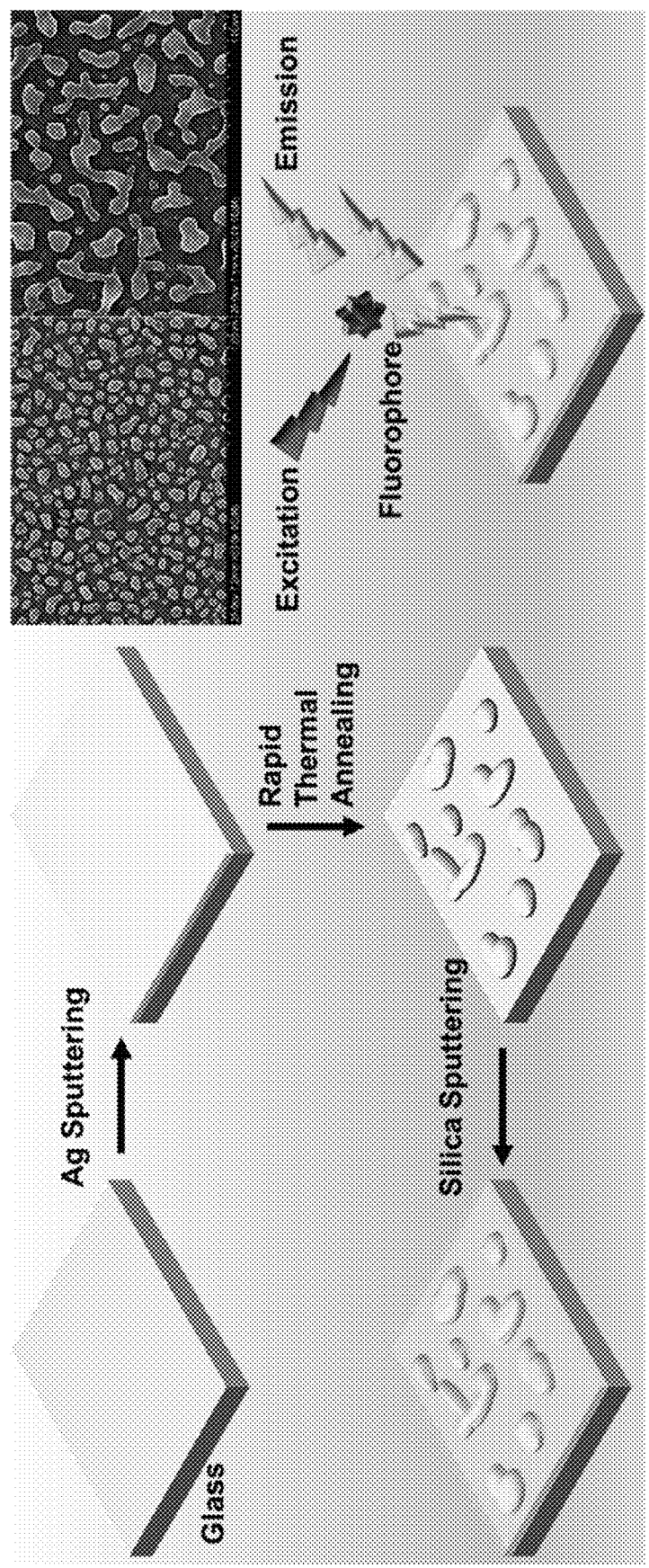
FIG. 4B is a diagram illustrating fabrication of an exemplary RTA treated metallic nanostructure that is modified with fluorophore-conjugated antibodies in an exemplary immunosensing process in accordance with various embodiments of the present disclosure.

Accordingly, as stated above, a fabricated slide having metallic nanostructures can be modified and treated with antibodies conjugated with fluorophores, exposed to a tissue sample, and analyzed using fluorescence microscopy, as represented in FIG. 4B. In brief, the figure shows the deposition of silver (Ag) film on a glass substrate via sputtering; the silver film undergoing rapid thermal annealing (RTA) to form silver nanostructures, and the coating of the silver nanostructures with silica via sputtering. Thus, the silica coated silver nanospheres on the glass substrate can be prepared for fluorescence immunoassays, such that fluorophore-conjugated antibodies can be applied to the slide, excited with a light source; and a fluorescence signal emitted by the fluorophore-conjugated antibodies excited by the light source can be detected using fluorescence microscopy, wherein an intensity of the fluorescence signal is amplified by the silica coated silver nanostructures.

Figure 5A:
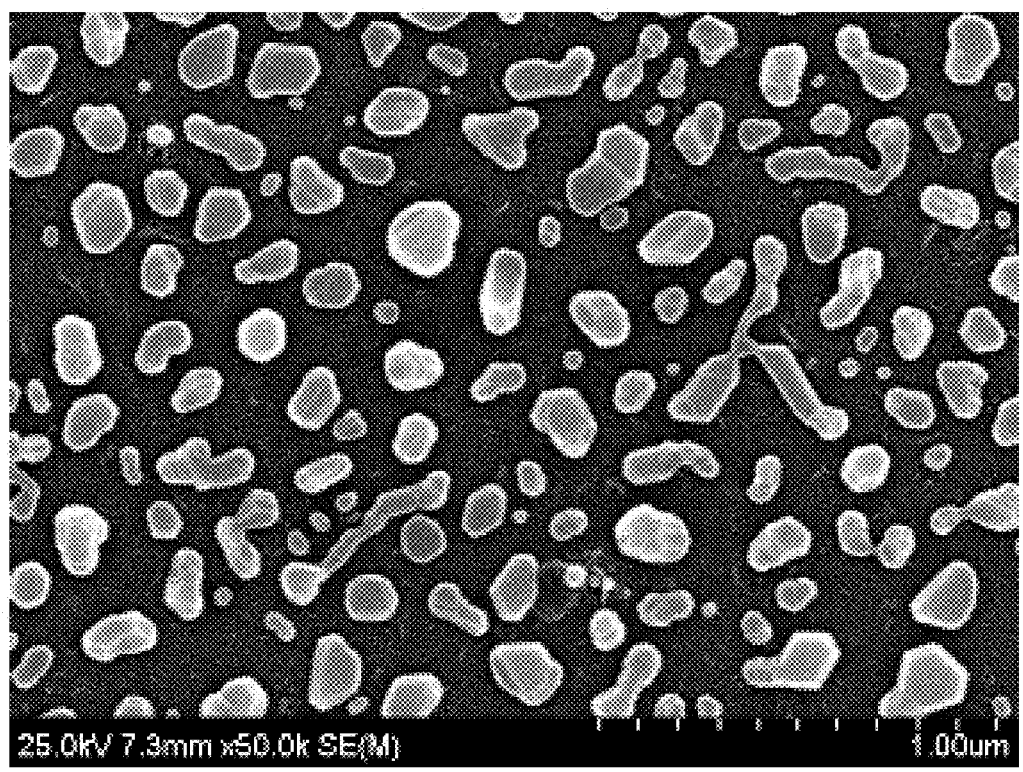
FIGS. 5A-5B are scanning electron microscope (SEM) images of annealed 125 Å film having (FIG. 5A) gold and (FIG. 5B) silver nanoparticles in accordance with the present disclosure.
Figure 5B:
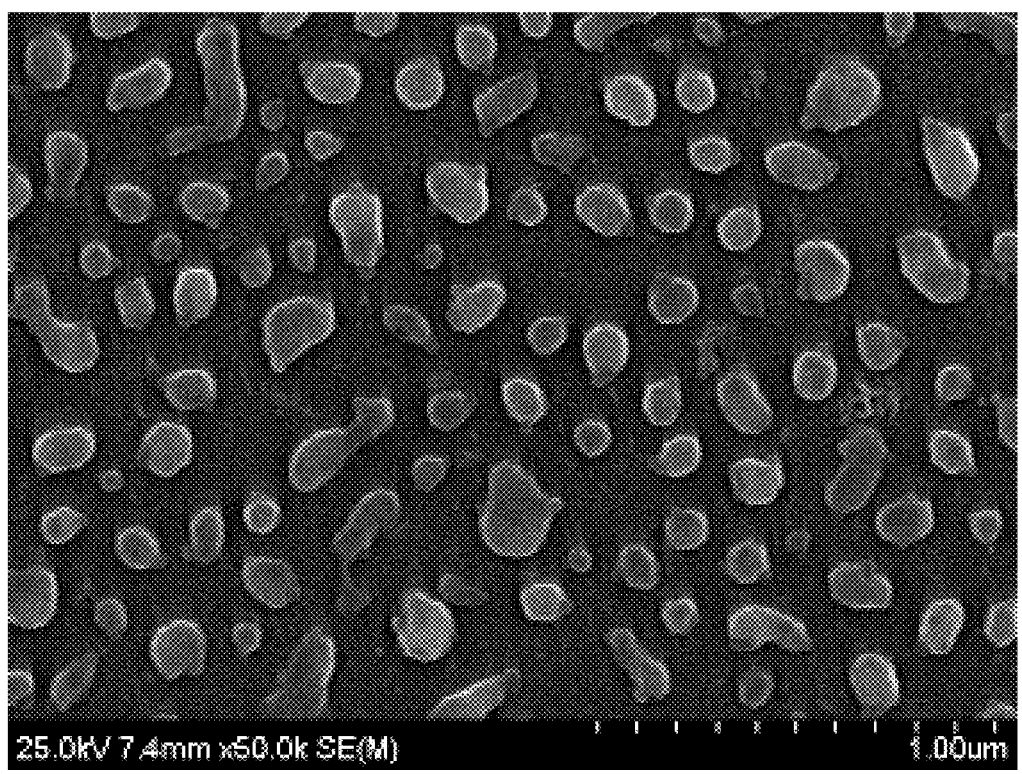

To understand the RTA process and fluorescence enhancement better, gold and silver were deposited on the glass slides with the same deposition (E-beam evaporation) and thermal annealing processes. The film thickness was 125 Å. FIGS. 5A-5B shows SEM images of the gold and silver nanoparticles (scale bar is 1 micron). No significant differences in distribution are apparent between the 2 metals.

Figure 6A:
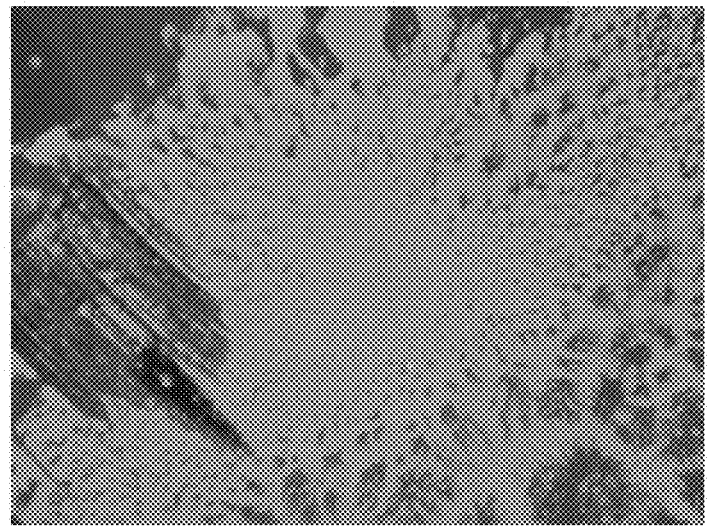
FIGS. 6A-6C show fluorescence intensity enhancement from (FIG. 6A) silver nanoparticles and (FIG. 6B) gold nanoparticles compared to that from (FIG. 6C) bare glass in accordance with the present disclosure.
Figure 6B:
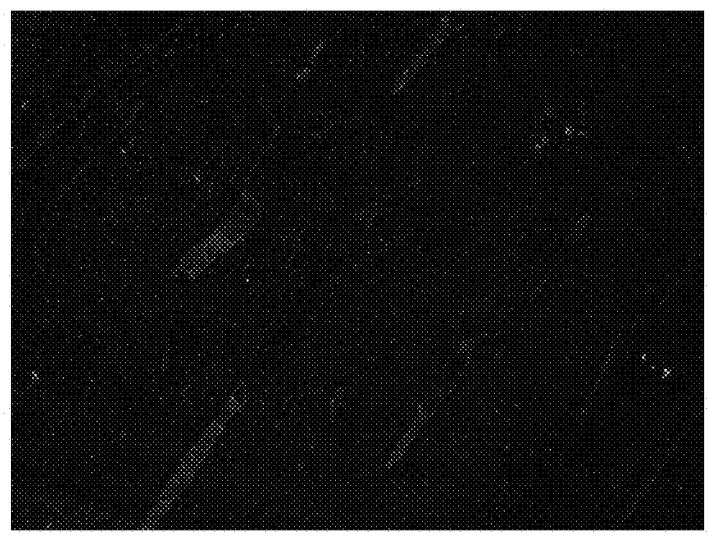
Figure 6C:
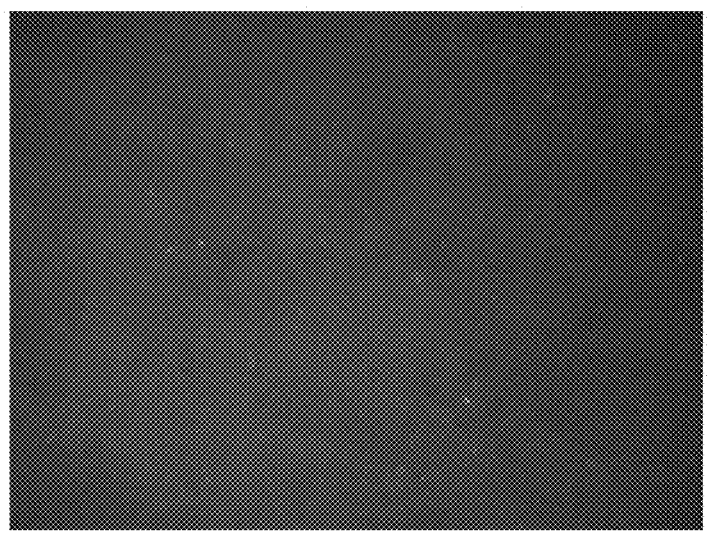

A Nikon FN1 fluorescence microscope was used to measure the fluorescence intensity. The microscope light dose was set to 100% of the solar light source with exposure time of 10 seconds and a gain of 1×. The solar light was filtered through a blue light filter as the excitation light. The emission light was filtered through a green light filter as the detection signal. The fluorescence images were collected and the green channel values of the RGB system (255,255, 255) were calculated. The fluorescence results clearly show that the gold nanoparticles quench, and silver particles enhance fluorescence intensity, compared to the intensity from a glass slide. This quenching from gold nanoparticles is expected and is a result of the non-radiative energy transfer from the excited states of the fluorophores to the gold particles[29-30]. FIGS. 6A-6C show fluorescence intensity enhancement from (A) silver nanoparticles and (B) gold nanoparticles compared to that from (C) bare glass. The metallic layers were deposited using E-beam evaporation and light source dose was set to 100%. As illustrated in the figures (which are originally represented as color images), the silver nanoparticles significantly increased the fluorescence intensity almost up to 255.

Figure 7A:
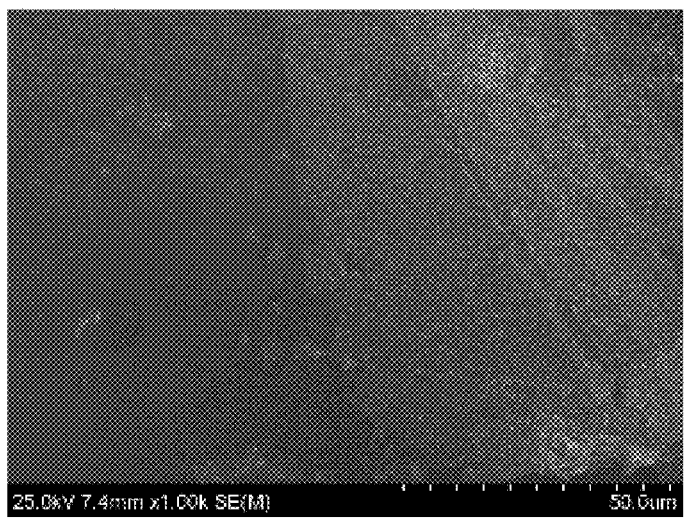
FIG. 7A shows an SEM image of silver nanopatterns via electron beam (E-beam) evaporation after a rising process in accordance with various embodiments of the present disclosure.
Figure 7B:
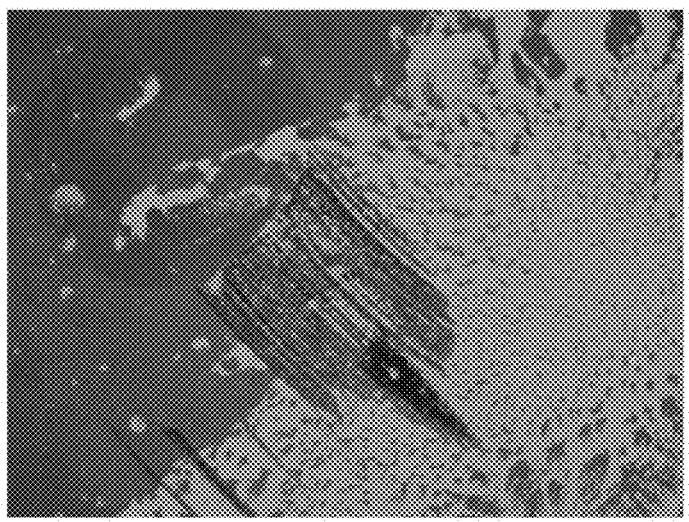
FIGS. 7B-7C show fluorescence images of silver nanopatterns via (FIG. 7B) E-beam evaporation and (FIG. 7C) sputter deposition in accordance with various embodiments of the present disclosure.
Figure 7B:
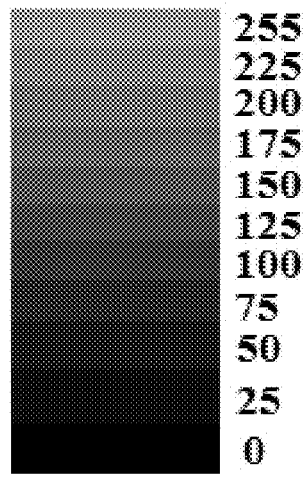
Figure 7C:
Figure 7C:
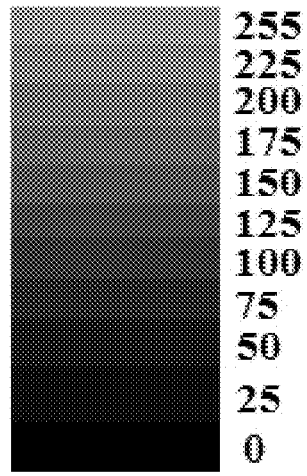
Figure 8A:
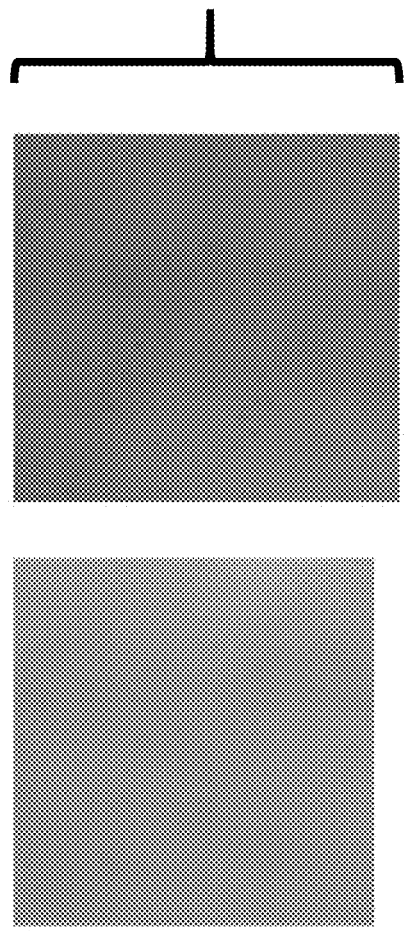
FIGS. 8A-8D show photographs of glass slides before (top) and after (bottom) an RTA process for sputter deposited films of thickness.
Figure 8B:
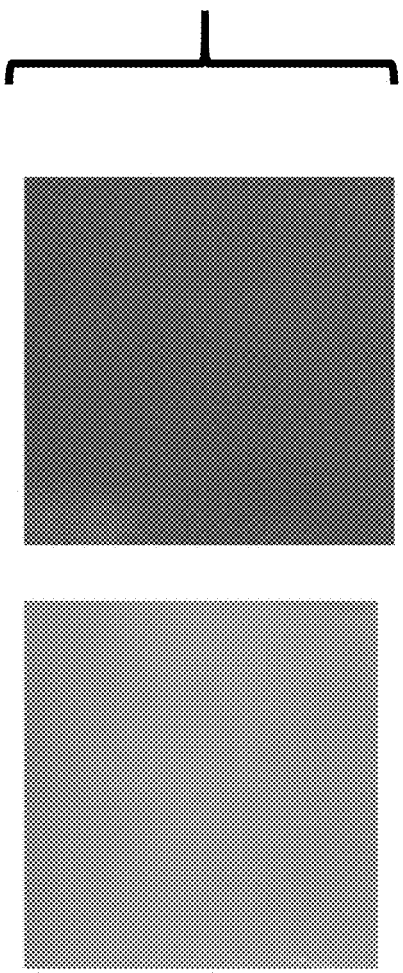
Figure 8C:
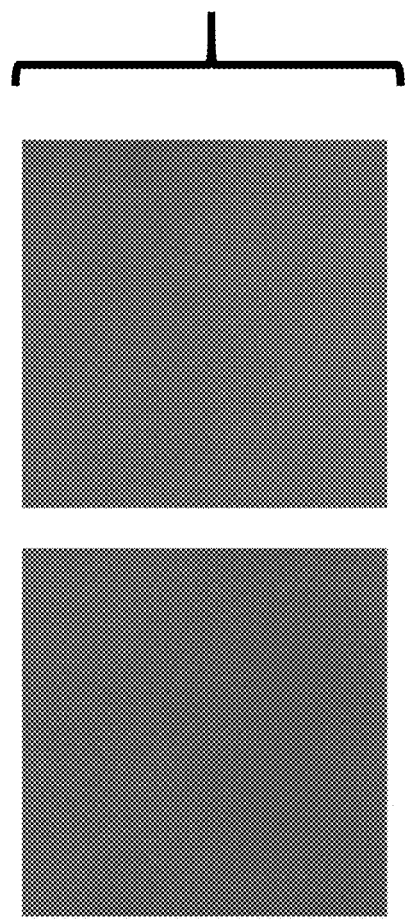
Figure 8D:
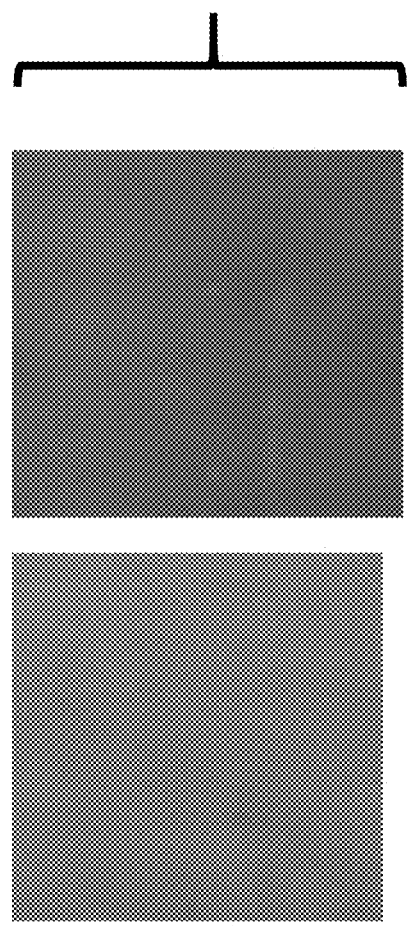

For deposition process comparison, the silver thin films were deposited using E-beam evaporation and sputtering. The resulting nanostructures were then compared using SEM and fluorescence microscopy. SEM images (which are originally represented as color images) of the annealed nanopatterns from these two methods show no visible difference, but as shown in FIG. 7A, after soaking and washing multiple times during the surface modification processes, the E-beam samples showed poorer adhesion to the surface. The area where the nanopatterns are absent exhibits much weaker fluorescence intensity, as shown in FIG. 7B. The sputtered silver sample has better adhesion with the glass surface, as shown in FIG. 7C; hence, sputtering was utilized as the deposition method in the further analysis of the present disclosure.

Evaluations were performed to consider whether RTA could significantly change surface characteristics of the silver film. Accordingly, FIGS. 8A-8D show photographs of glass slides before (top row) and after (bottom row) the RTA process for sputter deposited films of thickness: (FIG. 8A) 5 nm; (FIG. 8B) 10 nm; (FIG. 8C) 15 nm; (FIG. 8D) 25 nm in accordance with the present disclosure.

Figure 9:
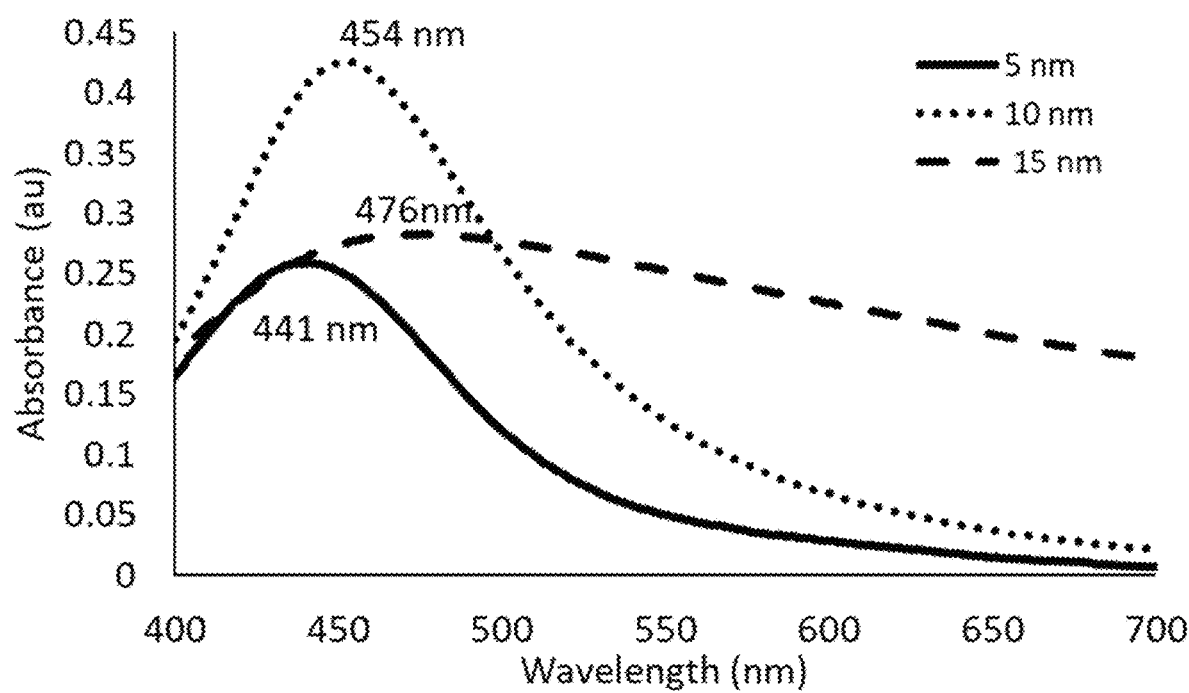
FIG. 9 shows a graph of UV-vis absorbance spectra of RTA treated silver nanopatterns of deposition thickness 5 nm, 10 nm, and 15 nm in accordance with the present disclosure.

The 5 nm, 10 nm, 15 nm, and 25 nm films presented different colors due to differences in light scattering and absorption[31-32]. It is noted that the annealed nanoparticle sizes are highly correlated to the film thickness. The thicker layers can generate larger size particles, and have longer and border wavelength absorption spectrum peak[33]. However, once the silver layer was over-deposited (thicker than 25 nm), the film lost the ability to transform into nanostructures, which shows the mirror effect rather than surface plasmon effect. As seen from the UV-vis absorbance peaks in FIG. 9, the wavelength of the absorbance peak red shifts from 441 nm to 476 nm and becomes wider with increase in the deposited film thickness.

Figure 10A:
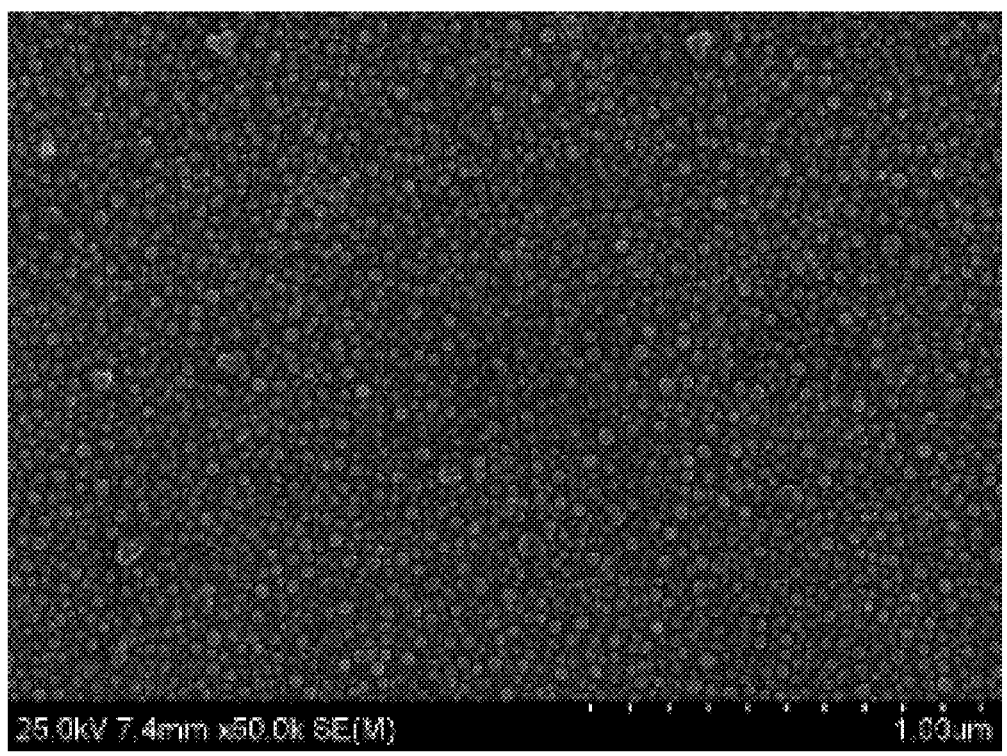
FIGS. 10A-10D show SEM images of annealed silver films deposited using sputtering at various layer thicknesses.
Figure 10B:
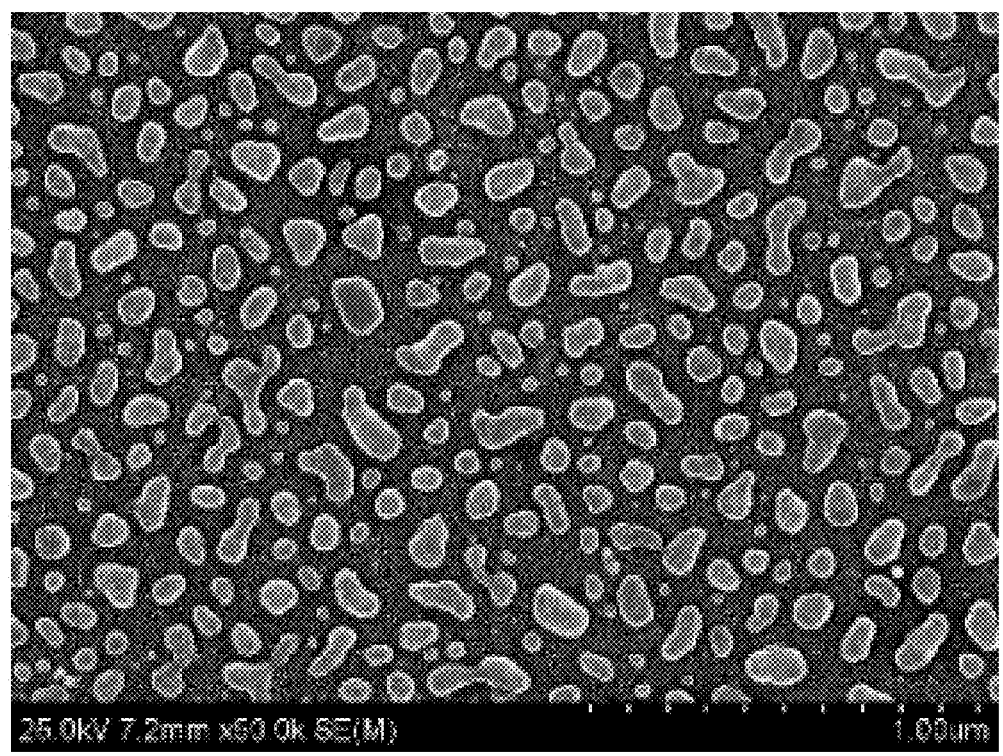
Figure 10C:
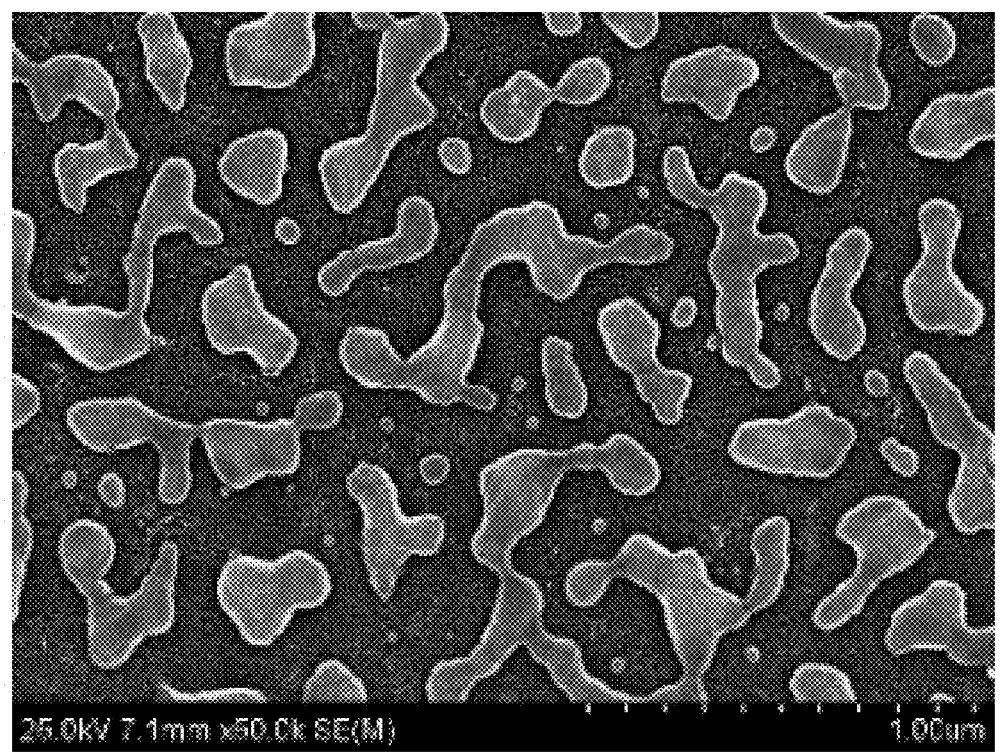
Figure 10D:
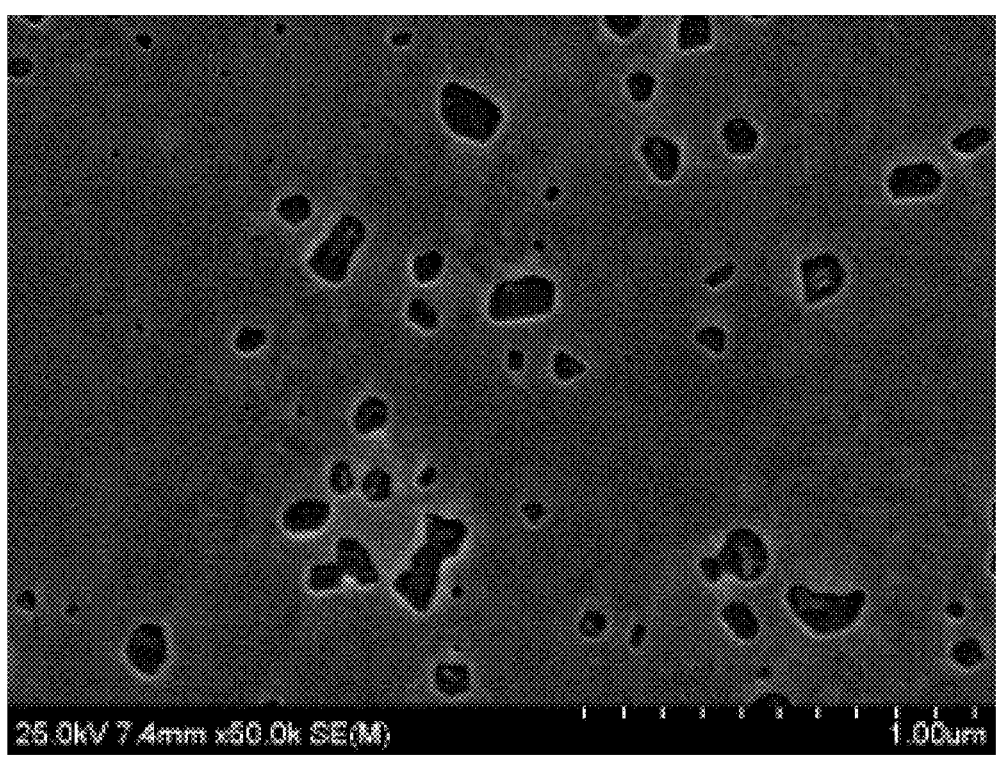
Figure 11A:
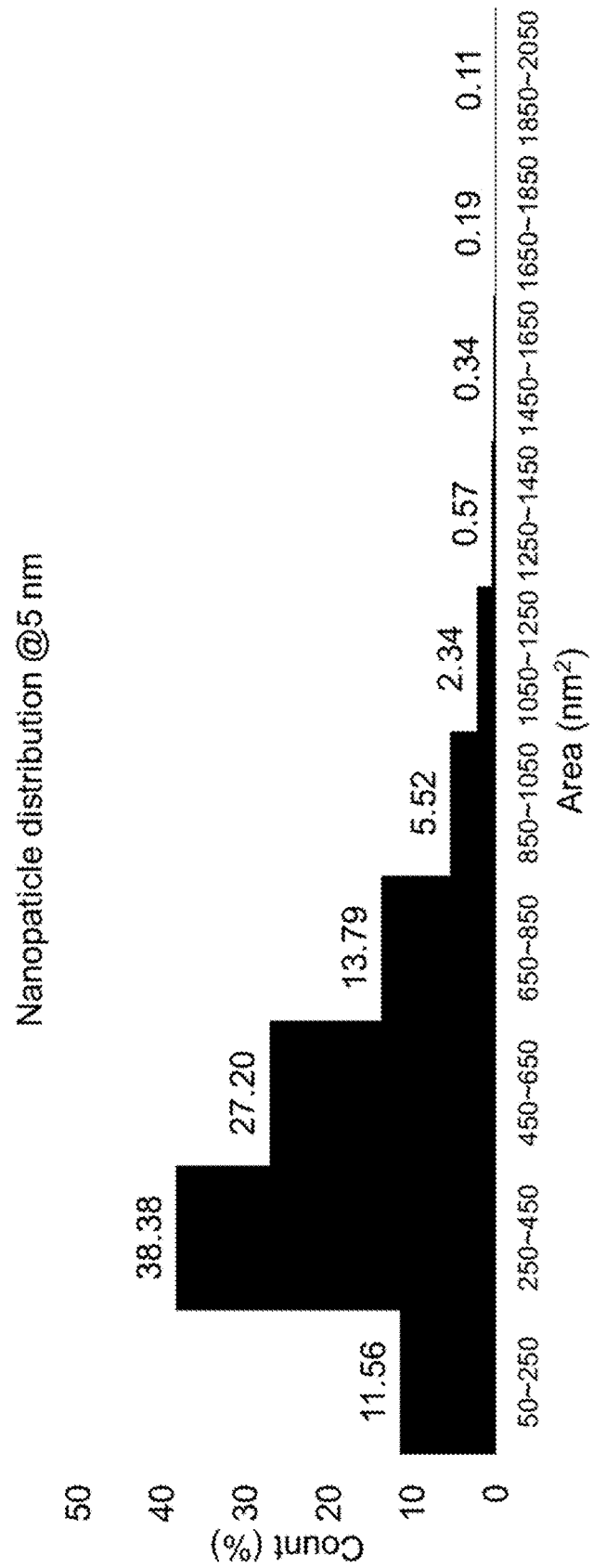
FIGS. 11A-11C show area distribution charts of RTA treated silver nanostructures for deposition thicknesses of (FIG. 11A) 5 nm, (FIG. 11B) 10 nm, and (FIG. 11C) 15 nm in accordance with the present disclosure.
Figure 11B:
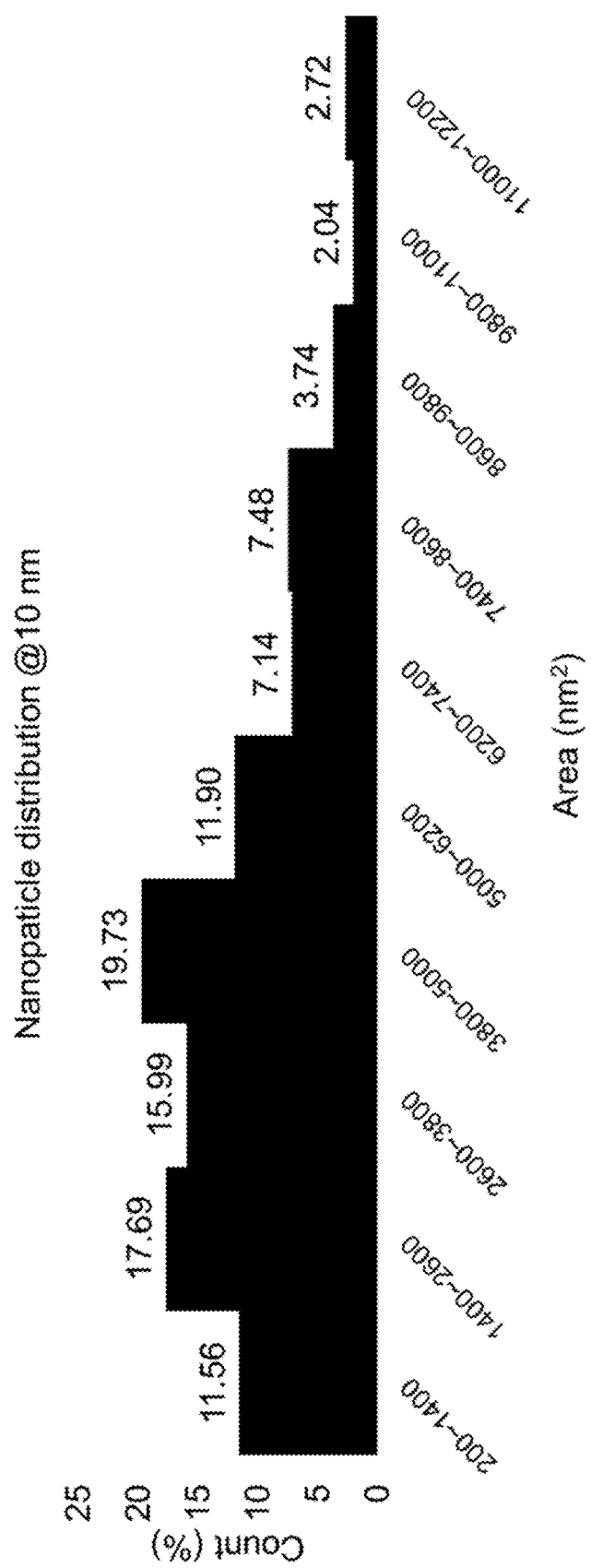
Figure 11C:
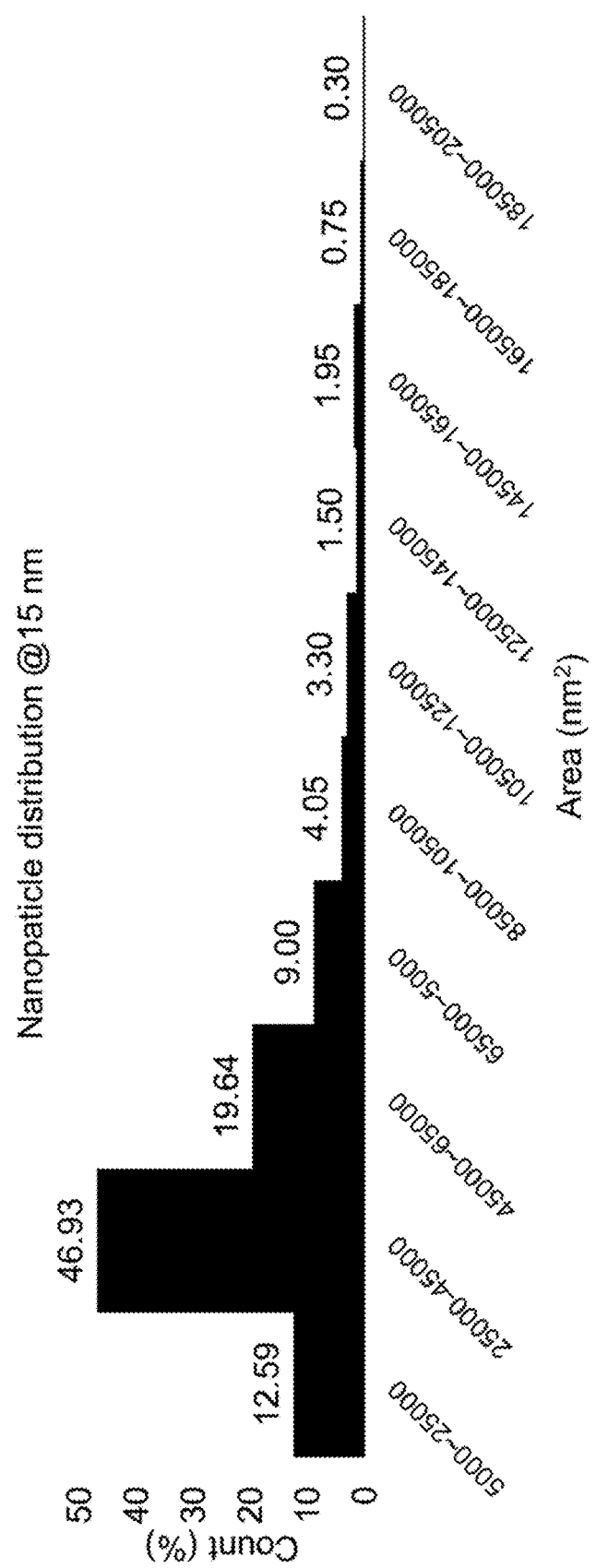

FIGS. 10A-10D show SEM images (scale bar is 1 micron) of annealed silver films deposited using sputtering at various layer thicknesses: (FIG. 10A) 5 nm; (FIG. 10B) 10 nm; (FIG. 10C) 15 nm; and (FIG. 10D) 25 nm. As shown in FIGS. 10A-10C, the thin silver film can produce isolated nanoislands on the glass surface. The 5 nm silver layer created hemi-spherical nanopatterns, densely spreading on the entire glass slide. For larger thicknesses, the nanopatterns changed into ellipsoidal or peanut-shaped structures. When the thickness reached 15 nm, worm or lace-like patterns appeared. The pattern lost its isolation when the thickness got up to 25 nm, resulting in a flat film layer without nanostructures, as illustrated in FIG. 10D.

The particles size, area density, and distribution of the 5 nm, 10 nm, and 15 nm silver samples were calculated and are shown in Table 1 (below). Because the thermal annealing cannot generate regular nanostructures, such as spheres and cubes, the area size was calculated to analyze the particle distribution. The particle density was found to decrease with increasing film thickness. The annealing treatment was observed to create nanopatterns with area with and without silver coating. However, the ratio of the covered area does not change significantly, at ~30%. Since the total volume of the deposited silver is constant, the average height of the annealed nanopatterns can be $$\text{Average height} = \frac{\text{Film thickness}}{\text{Covered area fraction}}. \quad (4)$$

TABLE 1

Nanoparticle characteristics for different deposited film thickness

| Film thickness (nm) | 5 | 10 | 15 |
|---|---|---|---|
| Cover area percent (%) | 29.8 | 32.2 | 31.4 |
| Area density (/μm$^2$) | 580 | 66.0 | 5.9 |
| Average height (nm) | 16.8 | 31.0 | 47.5 |

The nanoparticle area distributions are shown in FIGS. 11A-11D. About 39% of the particles from the 5 nm annealed film have areas in the range of range 250-450 nm$^2$ which is equal to 18-24 nm diameter if considered as spherical in shape. 47% of the particles from 15 nm film have areas in the range of 0.025-0.045 μm$^2$, 100 times larger than those of the 5 nm film. From these histograms, it can be concluded that the particle size increases with film thickness. Thus, thinner film can provide a better monochromaticity with a narrower distribution.

RTA annealed silver nanopatterns formed from the 5 nm, 10 nm, 15 nm, and 25 nm thick films were tested for fluorescence immunoassay detection and compared with the glass surface tests. The fluorescence intensities of each sample were detected under 4% and 100% of light source dose. The results are summarized in FIG. 12 and indicate that the 10 nm and 15 nm silver samples have large fluorescence enhancement. Specifically, the glass surface sample showed fluorescence intensity of 5.62 (4% dose) and 76.15 (100% dose) of 255 units in RGB's green channel. Under 4% dose light source, the 10 nm and 15 nm nanostructures increased the fluorescence intensity by factors of 1.72 and 2.76, respectively. And, under 100% dose, these enhancement factors were 1.46 and 2.10, respectively.

Correspondingly, the 5 nm silver nanostructures have smaller enhancement factors of only about 1.29~1.40 fold. This indicates that the quantum yield enhancement factor is strongly dependent on the nanoparticle dimensions. The 25 nm film resulted in a fluorescence decrease, because the thick film cannot generate the nanostructures, indicating that the flat silver film has no MEF effect. Thus, the 10 nm and 15 nm film samples were selected for the next step, in which SiO$_2$ was deposited on these particles.

Figure 13A:
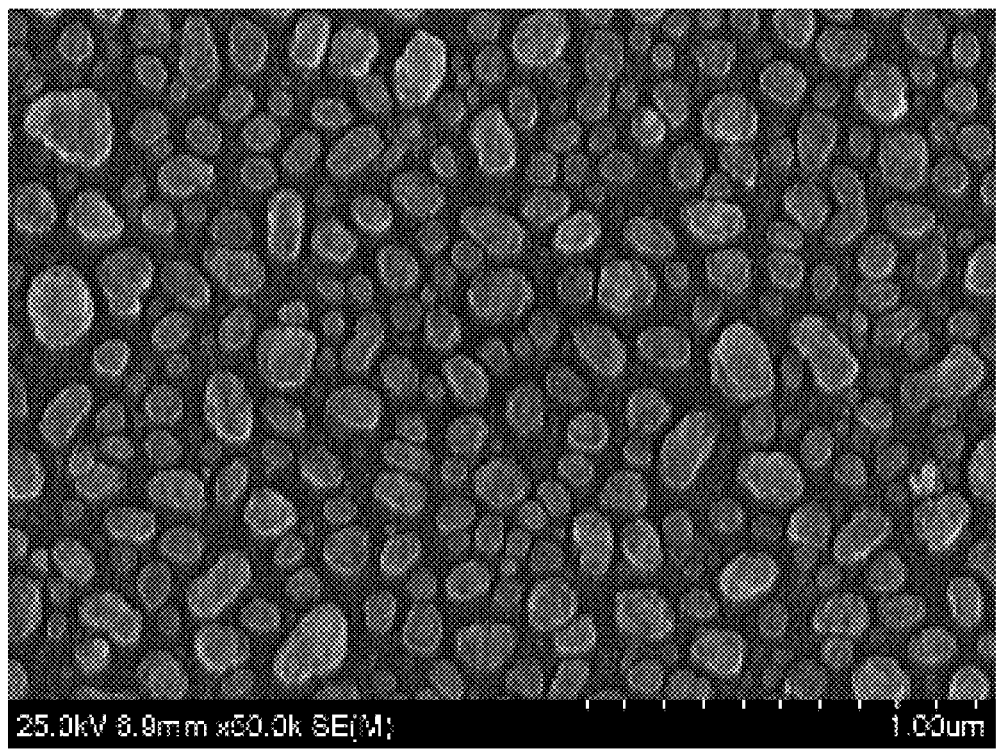
FIGS. 13A-13B show SEM images of silver nanoparticles after $SiO_2$ deposition of thickness (FIG. 13A) 5 nm and (FIG. 13B) 10 nm in accordance with the present disclosure.
Figure 13B:
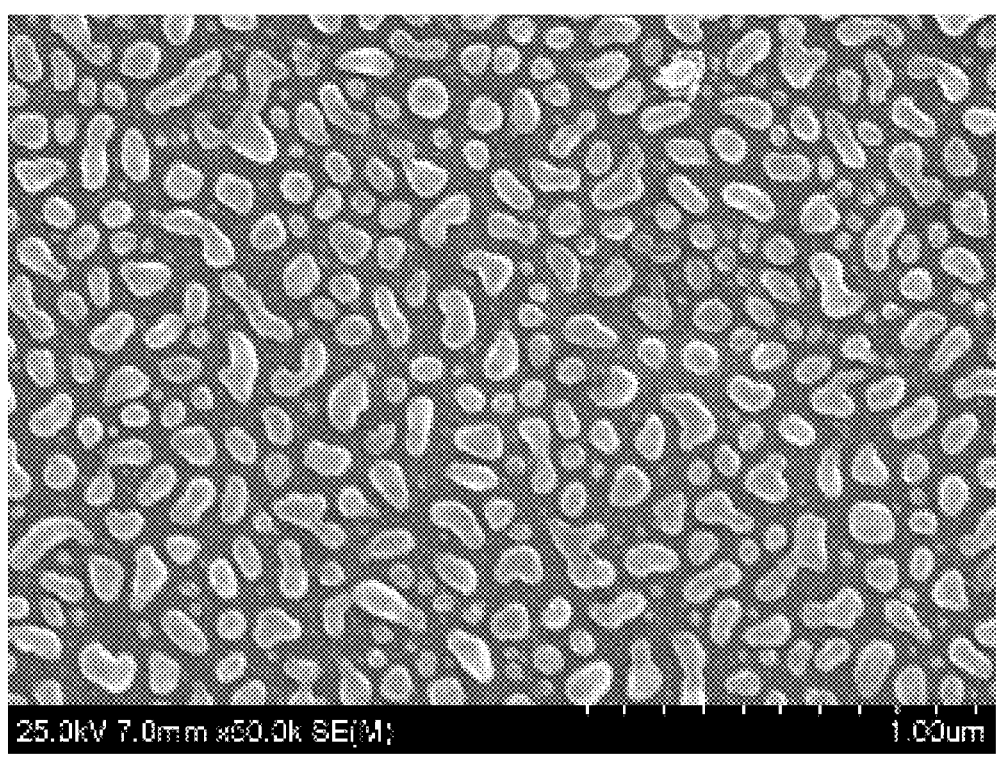

FDTD simulations of a computational model of an exemplary RTA treated metallic nanostructure indicate that a silica layer red shifts the plasmonic absorption peak close to the emission wavelength of the fluorophore and that the enhancement factors are dependent on the fluorophore-nanoparticle distance. While the sputter deposition generated structures adhere to the substrate better than those generated by E-beam deposition, the silica overlayer stabilizes the nanostructures through the sensing process. For these reasons, the effect of silica overlayer was investigated on MEF for the structures generated from the 10 nm and 15 nm films, in which deposition thicknesses of 5 nm and 10 nm were utilized. FIGS. 13A-13B show SEM images (scale bar is 1 micron) of silver nanoparticles after SiO$_2$ deposition of thickness (FIG. 13A) 5 nm and (FIG. 13B) 10 nm in accordance with the present disclosure. These particles were generated from the 10 nm silver film, and the figures shows that the nanopatterns are retained after SiO$_2$ sputtering.

In accordance with various embodiments of the present disclosure, four chips with silica coated nanostructures were utilized in fluorescence immunoassays: 10 nm silver RTA treated chip with 5 nm SiO$_2$ layer (10 nm Ag @ 5 nm SiO$_2$), 10 nm silver RTA treated chip with 10 nm SiO$_2$ layer (10 nm Ag @ 10 nm SiO$_2$), 15 nm silver RTA treated chip with 5 nm Ag @ 5 nm SiO$_2$), and 15 nm silver RTA treated chip with 10 nm SiO$_2$ layer (15 nm Ag @ 10 nm SiO$_2$). It was found that the samples were overexposed under 100% dose during fluorescence measurement, which means the SiO$_2$ layer increases the fluorescence intensity significantly. Thus, the light source dose was set to 4% for all reported measurements.

Figure 12:
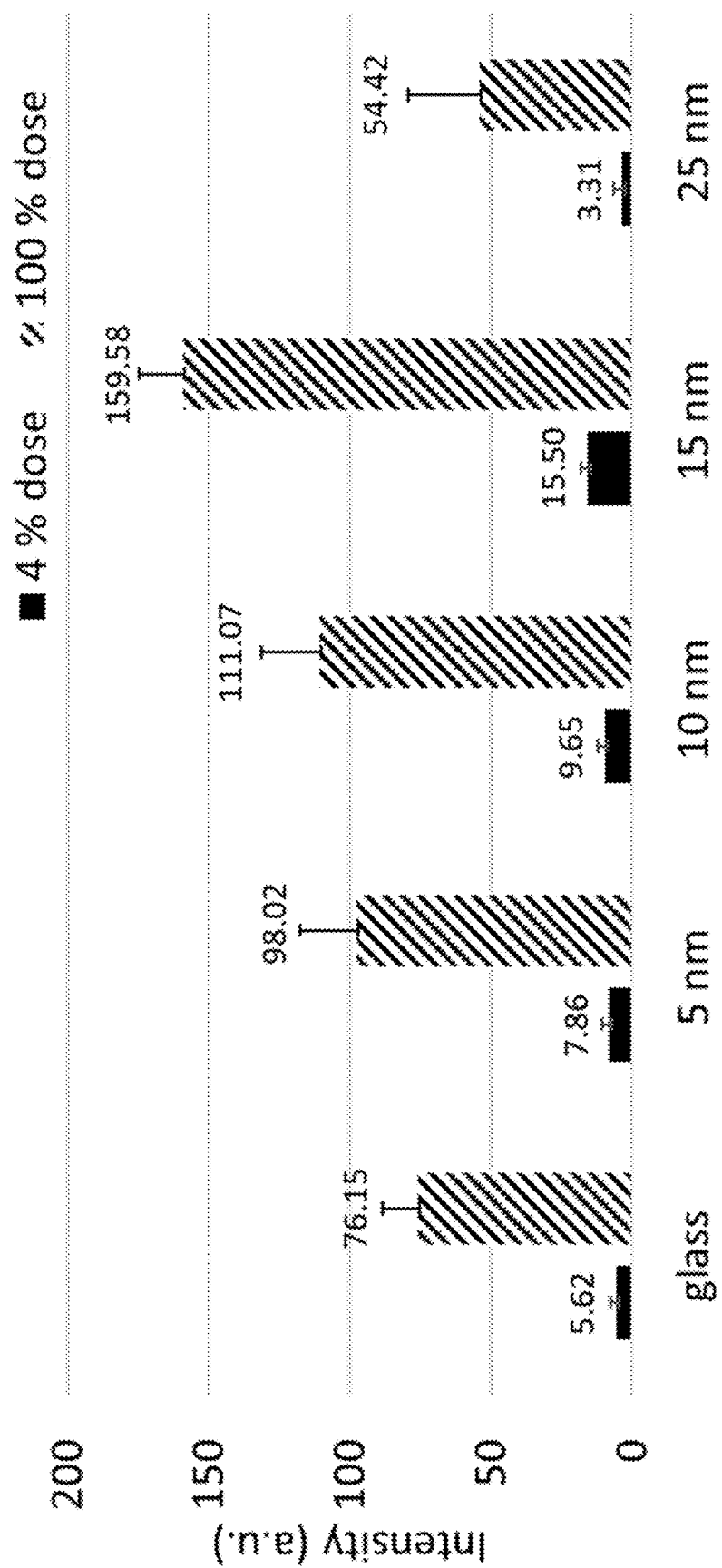
FIG. 12 shows a chart of the enhancement of fluorescence intensity from silver nanoparticles at deposition thicknesses of 5 nm, 10 nm, 15 nm, and 25 nm compared to that from a glass slide in accordance with the present disclosure.
Figure 14A:
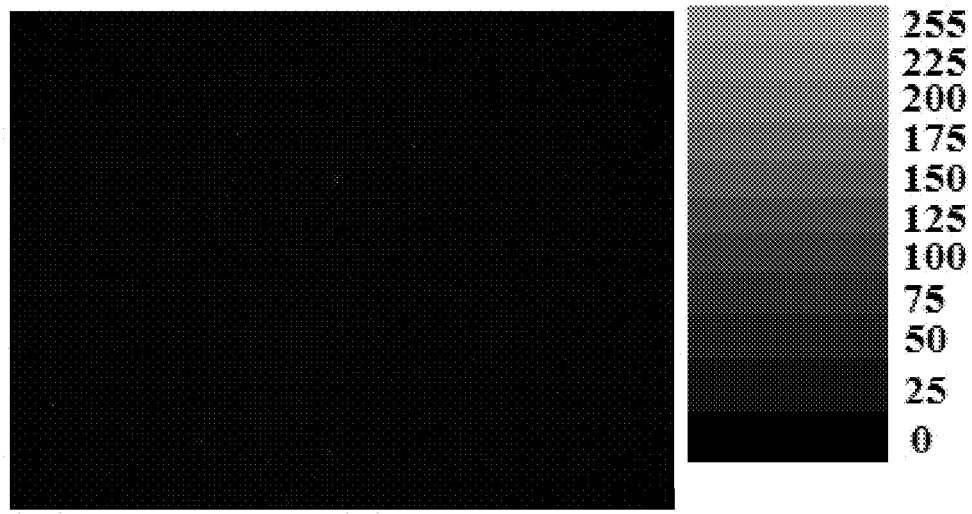
FIGS. 14A-14E show fluorescence images of (FIG. 14A) glass slide.
Figure 14B:
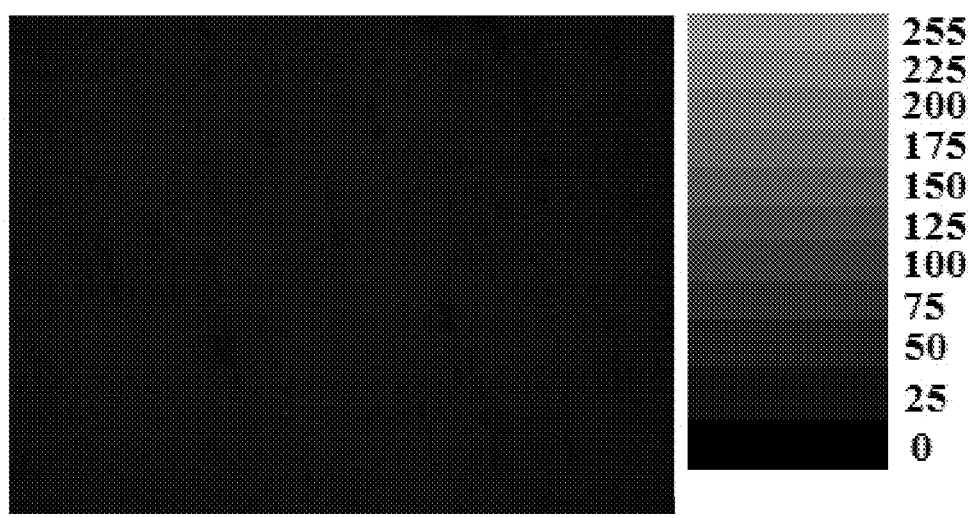
Figure 14C:
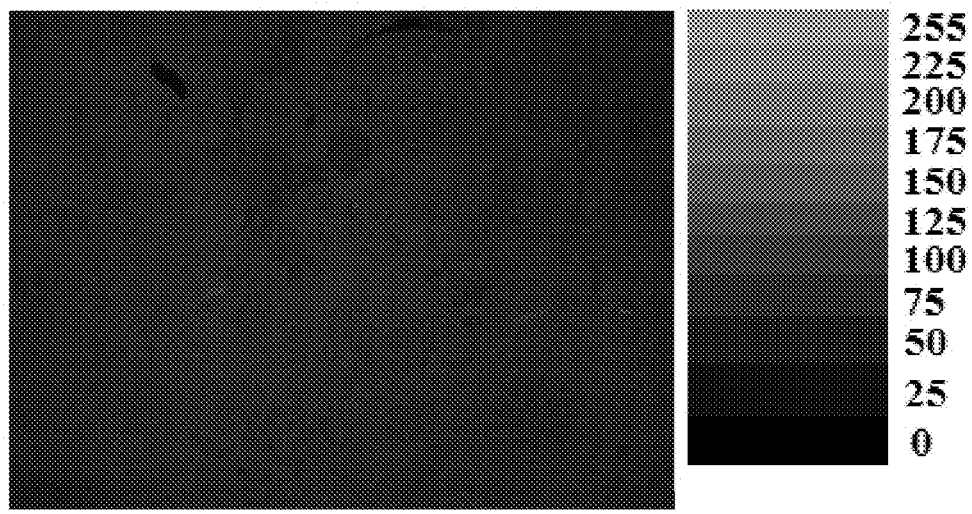
Figure 14D:
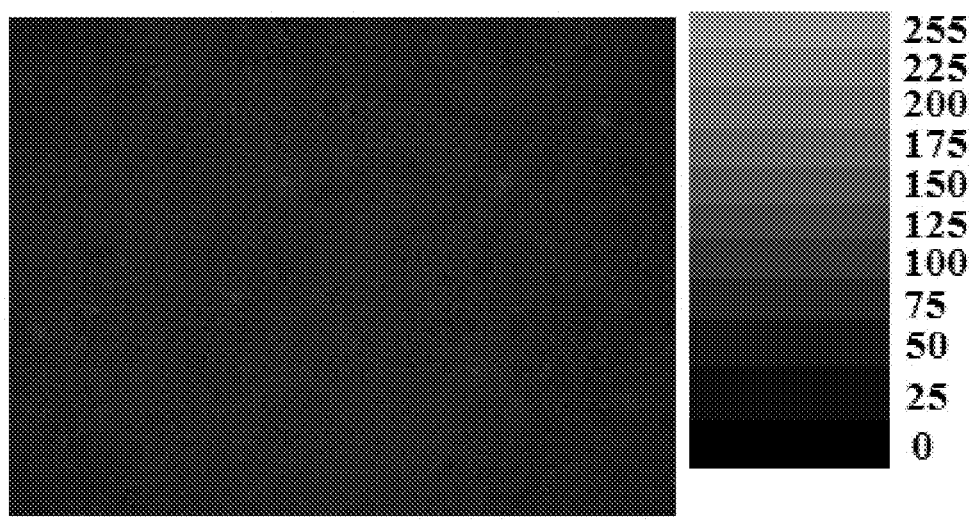
Figure 14E:
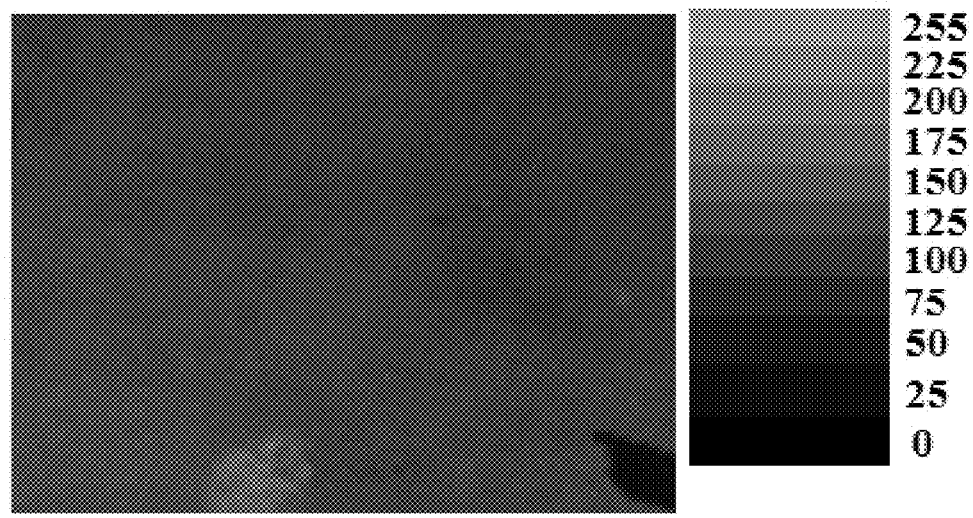
Figure 14F:
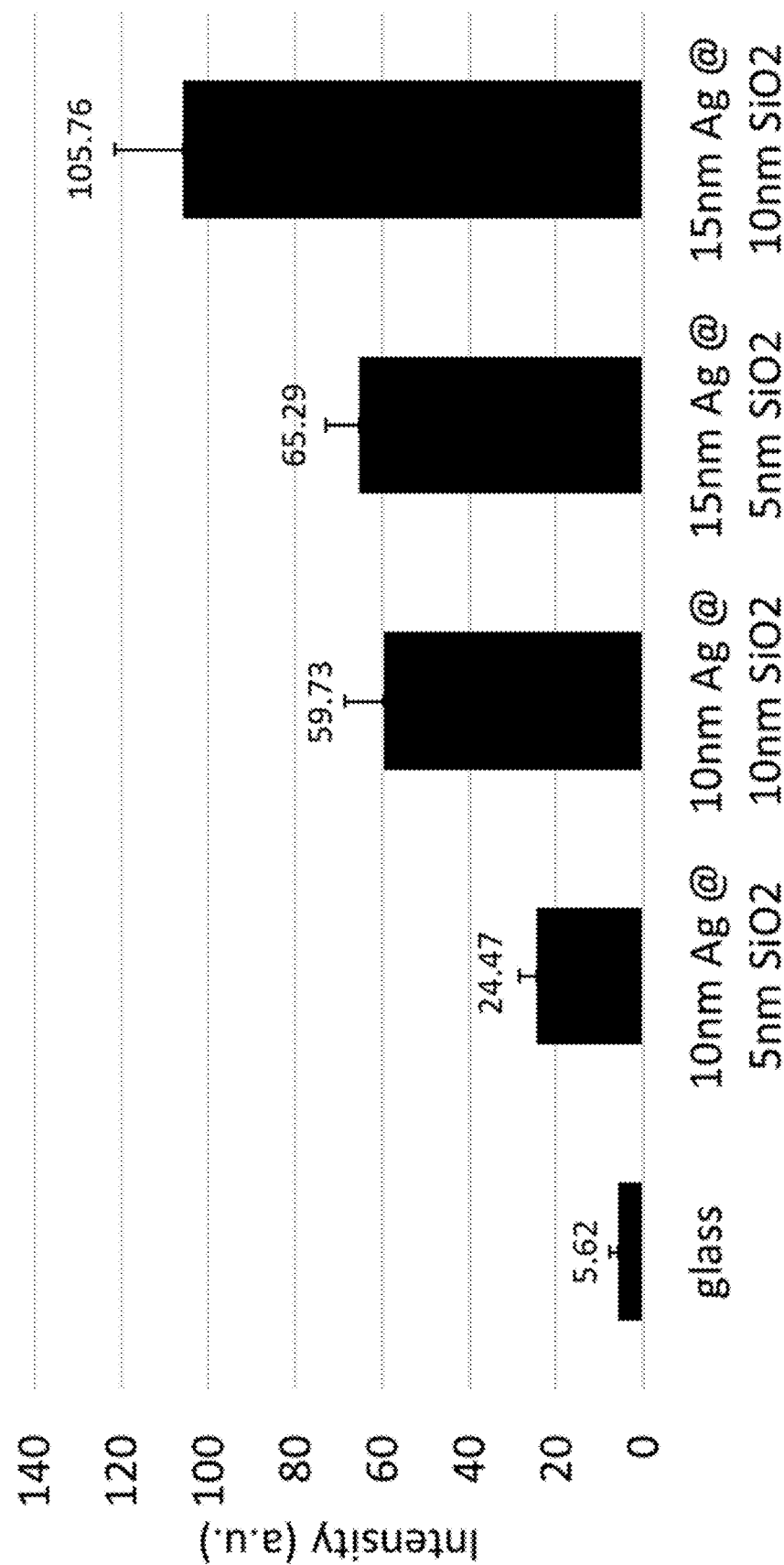
FIG. 14F shows histograms of fluorescence intensity from the samples of FIGS. 14A-14E.

The fluorescence images (which are originally represented as color images) of the glass surface sample (without any nanopatterns) and the four silica coated nanostructure samples are shown in FIGS. 14A-14E. All four silica coated nanostructures show larger fluorescence enhancement compared to the glass slide without any nanopatterns, and to the Ag structures without the silica coating. Comparison of intensities at 4% light source intensity from FIGS. 12 and 14F show that the SiO$_2$ coating provides additional enhancement factors of 2.53 for the 10 nm Ag @ 5 nm SiO$_2$, 4.21 for the 15 nm Ag @ 5 nm SiO$_2$, 6.19 for the 10 nm Ag @ 10 nm SiO$_2$, and 6.82 for the 15 nm Ag @ 10 nm SiO$_2$.

It would appear that precise control of distance between the fluorophore and silver nanoparticles is capable of improving enhancement factors, in addition to the effect of the dielectric coating on plasmonic phenomenon. Each modification layer on the glass chip is a well-established self-assembly monolayer. The APTES film would be of about 7 Å per monolayer[34-35]; however, the APTES film is usually multilayered and is of 2-5 nm thickness in realistic modifications[36-37]. The protein A of 42 kDa molecule weight has a rough diameter of 4-5 nm[38]. The IgG has a special Y shape with a height of 2-4 nm and cross section size/diameter of 20-40 nm[39-41]. The average distance from the silver surface to the fluorophore is about 20-28 nm including the ~10 nm from the added SiO$_2$ layer. In addition, the SiO$_2$ coating introduces a red shift to the plasmonic peak to near the emission peak of the fluorophore, thus increasing the enhancement factor. For this particular immunofluorescence assay, the 15 nm Ag @10 nm SiO$_2$ samples achieved the maximum enhancement factor of 18.81 to the glass surface sample. These results indicate the potential for further optimization and the ability for the rational design of the largest possible MEF effect for immunoassays.

Figure 15:
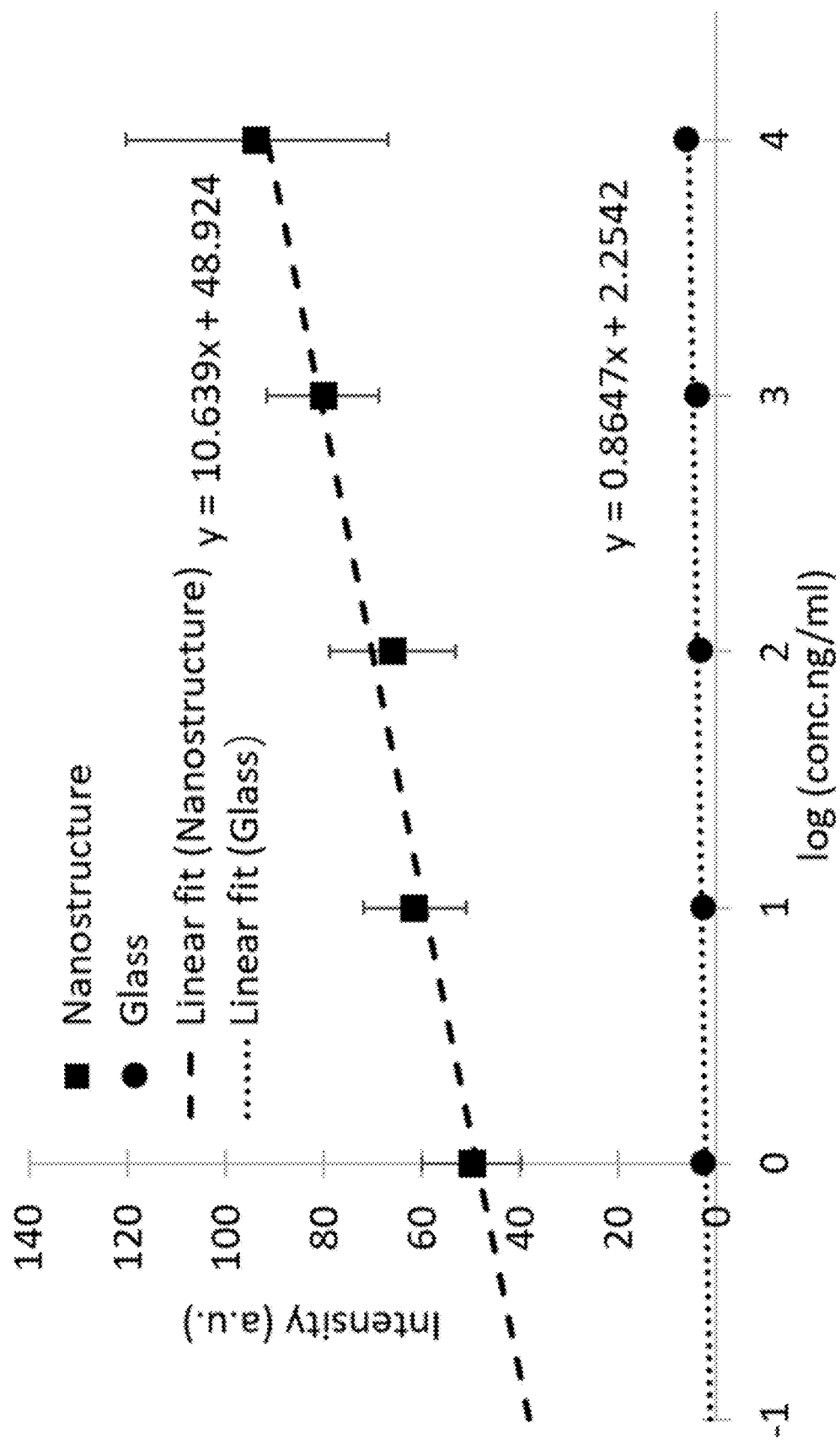
FIG. 15 shows calibration curves of glass and 15 nm Ag @ 10 nm $SiO_2$ nanostructured sensors in accordance with the present disclosure.

Sensor calibration curves for a bare glass side and the 15 nm Ag @ 10 nm SiO$_2$ sample were constructed and are shown in FIG. 15. Fluorescence intensity is linear in log (concentration) (ng/mL) over the range of 1-10,000 ng/ml. Sensitivity of the sensor with nanostructures is calculated to be above 12.3 times larger than that without, due to MEF. These results indicate that the nanostructure MEF device has the potential of achieving sub ng/ml limits of detection in realistic cancer marker assays.

Considering the easy, fast, and inexpensive fabrication process, an exemplary RTA treated metallic nanostructure with silica coating layer is a competitive method amongst other various MEF strategies to improve immunofluorescence assays. A comparison of the enhancement provided by different MEF strategies from literature is given in Table 2 (below). These strategies are also classified by the complexity in processing and scaling. It is apparent that an exemplary method, in accordance with embodiments of the present disclosure, is capable of achieving one of the highest enhancement factors upon optimization using easy processing steps while being scalable. Although the comparison in Table 2 is useful, and brings out certain helpful features, true comparisons should be made on the basis of realized biosensors, and their performance, such as presented in the present disclosure. For example, the electron beam lithographic technique shows slightly larger enhancement factors than an exemplary technique of the present disclosure;

however, it is for ordered gold nanostructures coupled to CdS/ZnS nanocrystals dispersed as a polymer blend. Such a system is useful in lighting applications, but not for biosensing, such as for cancer markers, which necessitates the use of fluorophores conjugated to antibodies and overlap of the LSPR (localized surface plasmon resonance) peak with their emission frequency. Indeed, very large enhancement factors with polymer dispersed systems have been realized using Ag/Cu nanoparticles and Alexa fluorophores in previously reported studies[19-20]. It should also be recognized that MEF enhancement needs to translate to lowered LOD (limit of detection) and higher sensitivity for biosensor applications, as demonstrated in the present disclosure.

TABLE 2

Comparison of different MEF strategies.

| Method | Complexity | Large-scale fabrication | Enhancement factor |
|---|---|---|---|
| RTA-Silica | Easy | Yes | 18.81 |
| SiO$_2$-coated silver colloid[42] | Complicated | Yes | 10 |
| Surface-deposited silver nanoparticles[43] | Medium | Yes | 1.5-3 |
| Electron beam lithography[44] | Complicated | No | 21-36 |

In accordance with various embodiments of the present disclosure, an exemplary nanostructure fabrication process based on dewetting of thin silver films by rapid thermal annealing, which is suitable for large areas, is described. In such a process, the nanostructures can be coated with a thin silica film to protect them and to control the distance between the metallic surface and fluorophores. An analysis of the fluorescence enhancement from exemplary metallic nanostructures in accordance with embodiments of the present disclosure reveals nearly a 19-fold increase in the fluorescence intensity. Calibration of the resulting plasmonically enhanced immunofluorescence sensor shows that it is nearly 13 times more sensitive than the non-enhanced version and is capable of robust quantification of a biomarker at ~1 ng/ml levels.

Accordingly, the present disclosure presents a novel fabrication method to achieve large-area nanostructures using RTA and silica deposition for use in metal-enhanced fluorescence (MEF) immunoassays, in accordance with various embodiments. This method overcomes the drawbacks of other nanostructure fabrication processes, such as lithography-based non-scalable, and complicated processes. A rational process for optimizing the MEF effect is described based on FDTD calculations and physical reasoning. By optimizing the fluorophore-nanoparticle structure and the red shift of the plasmonic absorption peak using a SiO$_2$ overlayer, the fluorescence intensity was enhanced by a factor of 18.18 in a typical immunoassay utilizing IgGs. These results provide a great potential for exploiting MEF in practical biosensing applications It should be emphasized that the above-described embodiments are merely possible examples of implementations, merely set forth for a clear understanding of the principles of the present disclosure. Many variations and modifications may be made to the above-described embodiment(s) without departing substantially from the principles of the present disclosure. All such modifications and variations are intended to be included herein within the scope of this disclosure.

Unless otherwise specified or indicated by context, the terms "a", "an", and "the" mean "one or more." For example, "a molecule" should be interpreted to mean "one or more molecules."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion additional components other than the components recited in the claims. The term "consisting essentially of" should be interpreted to be partially closed and allowing the inclusion only of additional components that do not fundamentally alter the nature of the claimed subject matter.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

All references, including publications, patent applications, and patents, cited herein are hereby incorporated by reference to the same extent as if each reference were individually and specifically indicated to be incorporated by reference and were set forth in its entirety herein.

Preferred aspects of this invention are described herein, including the best mode known to the inventors for carrying out the invention. Variations of those preferred aspects may become apparent to those of ordinary skill in the art upon reading the foregoing description. The inventors expect a person having ordinary skill in the art to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

ABBREVIATIONS

MEF, metal-enhanced fluorescence;
RTA, rapid thermal annealing;
SEM, scanning electron microscopy;
FDTD, finite different time-domain;
IgG, immunoglobulin G;
BSA, bull serum albumin;
APTES, (3-aminopropyl)-triethoxy-silane.

REFERENCES

1. Demchenko, A. P., *Introduction to fluorescence sensing*. Springer Science & Business Media: 2008.
2. Aslan, K.; Gryczynski, I.; Malicka, J.; Matveeva, E.; Lakowicz, J. R.; Geddes, C. D., Metal-enhanced fluorescence: an emerging tool in biotechnology. *Current Opinion in Biotechnology* 2005, 16 (1), 55-62.
3. Anker, J. N.; Hall, W. P.; Lyandres, O.; Shah, N. C.; Zhao, J.; Van Duyne, R. P., Biosensing with plasmonic nanosensors. In *Nanoscience And Technology: A Collection of Reviews from Nature Journals*, World Scientific: 2010; pp 308-319.
4. Vo-Dinh, T., Surface-enhanced Raman spectroscopy using metallic nanostructures. *Trends in Analytical Chemistry* 1998, 17 (8), 557-582.
5. Zhang, X.; Liu, Z., Superlenses to overcome the diffraction limit. *Nature Materials* 2008, 7 (6), 435-441.
6. Geddes, C. D.; Lakowicz, J. R., Metal-enhanced fluorescence. *Journal of Fluorescence* 2002, 12 (2), 121-129.
7. Geddes, C. D.; Cao, H.; Gryczynski, I.; Gryczynski, Z.; Fang, J.; Lakowicz, J. R., Metal-enhanced fluorescence (MEF) due to silver colloids on a planar surface: Potential applications of indocyanine green to in vivo imaging. *The Journal of Physical Chemistry A* 2003, 107 (18), 3443-3449.
8. Lakowicz, J. R.; Shen, Y.; D'Auria, S.; Malicka, J.; Fang, J.; Gryczynski, Z.; Gryczynski, I., Radiative decay engineering: 2. Effects of silver island films on fluorescence intensity, lifetimes, and resonance energy transfer. *Analytical Biochemistry* 2002, 301 (2), 261-277.
9. Yue, W.; Wang, Z.; Yang, Y.; Chen, L.; Syed, A.; Wong, K.; Wang, X., Electron-beam lithography of gold nanostructures for surface-enhanced Raman scattering. *Journal of Micromechanics and Microengineering* 2012, 22 (12), 125007.
10. Seo, J.-H.; Park, J. H.; Kim, S.-I.; Park, B. J.; Ma, Z.; Choi, J.; Ju, B.-K., Nanopatterning by laser interference lithography: applications to optical devices. *Journal of Nanoscience and Nanotechnology* 2014, 14 (2), 1521-1532.
11. Zabila, Y.; Perzanowski, M.; Dobrowolska, A.; Kac, M.; Polit, A.; Marszalek, M., Direct laser interference patterning: theory and application. *Acta Physica Polonica—Series A General Physics* 2009, 115 (2), 591-593.
12. Konkola, P. T. Design and analysis of a scanning beam interference lithography system for patterning gratings with nanometer-level distortions. Massachusetts Institute of Technology, 2003.
13. Resnick, D. J.; Sreenivasan, S. V.; Willson, C. G., Step & flash imprint lithography. *Materials Today* 2005, 8 (2), 34-42.
14. Toma, M.; Loget, G.; Corn, R. M., Fabrication of broadband antireflective plasmonic gold nanocone arrays on flexible polymer films. *Nano Letters* 2013, 13 (12), 6164-6169.
15. Yu, Y.; Zhang, G., Colloidal Lithography. In *Updates in Advanced Lithography*, InTech: 2013.
16. Li, Y.; Shi, G., Electrochemical growth of two-dimensional gold nanostructures on a thin polypyrrole film modified ITO electrode. *The Journal of Physical Chemistry B* 2005, 109 (50), 23787-23793.
17. Liu, J.; Li, S.; Bhethanabotla, V. R. In *Metal-enhanced immunofluorescence assays for detection of carcinoembryonic antigen*, SENSORS, IEEE, 2017; pp 1-3.
18. Zhang, J.; Langille, M. R.; Mirkin, C. A., Photomediated synthesis of silver triangular bipyramids and prisms: the effect of pH and BSPP. *Journal of the American Chemical Society* 2010, 132 (35), 12502-12510.
19. Chowdhury, S.; Bhethanabotla, V. R.; Sen, R., Effect of Ag—Cu Alloy Nanoparticle Composition on Luminescence Enhancement/Quenching. *The Journal of Physical Chemistry C* 2009, 113 (30), 13016-13022.
20. Chowdhury, S.; Bhethanabotla, V. R.; Sen, R., Silver-copper alloy nanoparticles for metal enhanced luminescence. *Applied Physics Letters* 2009, 95 (13), 131115.
21. Liu, J.; Li, S.; Bhethanabotla, V. R., Integrating Metal-Enhanced Fluorescence and Surface Acoustic Waves for Sensitive and Rapid Quantification of Cancer Biomarkers from Real Matrices. *ACS Sensors* 2018, 3 (1), 222-229.
22. Alonzo-Medina, G. M.; González-Gonzalez, A.; Sacedón, J. L.; Oliva, A. I. In *Understanding the thermal annealing process on metallic thin films*, IOP Conference Series: Materials Science and Engineering, IOP Publishing: 2013; p 012013.
23. Srolovitz, D. J.; Goldiner, M. G., The thermodynamics and kinetics of film agglomeration. *JOM* 1995, 47 (3), 31-36.
24. Ruffino, F.; Grimaldi, M. G., Controlled dewetting as fabrication and patterning strategy for metal nanostructures. *physica status solidi (a)* 2015, 212 (8), 1662-1684.
25. Herminghaus, S.; Jacobs, K.; Mecke, K.; Bischof, J.; Fery, A.; Ibn-Elhaj, M.; Schlagowski, S., Spinodal Dewetting in Liquid Crystal and Liquid Metal Films. *Science* 1998, 282 (5390), 916.
26. Yadavali, S.; Khenner, M.; Kalyanaraman, R., Pulsed laser dewetting of Au films: Experiments and modeling of nanoscale behavior. *Journal of Materials Research* 2013, 28 (13), 1715-1723.
27. Hu, X.; Cahill, D. G.; Averback, R. S., Nanoscale pattern formation in Pt thin films due to ion-beam-induced dewetting. *Applied Physics Letters* 2000, 76 (22), 3215-3217.
28. Thompson, C. V., Solid-State Dewetting of Thin Films. *Annual Review of Materials Research* 2012, 42 (1), 399-434.
29. Dulkeith, E.; Morteani, A. C.; Niedereichholz, T.; Klar, T. A.; Feldmann, J.; Levi, S. A.; Van Veggel, F.; Reinhoudt, D. N.; Möller, M.; Gittins, D. I., Fluorescence quenching of dye molecules near gold nanoparticles: radiative and nonradiative effects. *Physical Review Letters* 2002, 89 (20), 203002.
30. Dulkeith, E.; Ringler, M.; Klar, T. A.; Feldmann, J.; Munoz Javier, A.; Parak, W. J., Gold nanoparticles quench fluorescence by phase induced radiative rate suppression. *Nano Letters* 2005, 5 (4), 585-589.
31. Liz-Marzán, L. M., Nanometals. *Materials Today* 2004, 7 (2), 26-31.
32. Hsu, C. W.; Zhen, B.; Qiu, W.; Shapira, O.; DeLacy, B. G.; Joannopoulos, J. D.; Soljačić, M., Transparent displays enabled by resonant nanoparticle scattering. *Nature Communications* 2014, 5, 3152.
33. Agnihotri, S.; Mukherji, S.; Mukherji, S., Size-controlled silver nanoparticles synthesized over the range 5-100 nm using the same protocol and their antibacterial efficacy. *RSC Advances* 2014, 4 (8), 3974-3983.
34. Howarter, J. A.; Youngblood, J. P., Optimization of silica silanization by 3-aminopropyltriethoxysilane. *Langmuir* 2006, 22 (26), 11142-11147.
35. Vandenberg, E. T.; Bertilsson, L.; Liedberg, B.; Uvdal, K.; Erlandsson, R.; Elwing, H.; Lundström, I., Structure of 3-aminopropyl triethoxy silane on silicon oxide. *Journal of Colloid and Interface Science* 1991, 147 (1), 103-118.

36. Wang, Y.-P.; Yuan, K.; Li, Q.-L.; Wang, L.-P.; Gu, S.-J.; Pei, X.-W., Preparation and characterization of poly (N-isopropylacrylamide) films on a modified glass surface via surface initiated redox polymerization. *Materials Letters* 2005, 59 (14-15), 1736-1740.
37. Kim, J.; Seidler, P.; Wan, L. S.; Fill, C., Formation, structure, and reactivity of amino-terminated organic films on silicon substrates. *Journal of Colloid and Interface Science* 2009, 329 (1), 114-119.
38. Erickson, H. P., Size and shape of protein molecules at the nanometer level determined by sedimentation, gel filtration, and electron microscopy. *Biological Procedures Online* 2009, 11 (1), 32-51.
39. Droz, E.; Taborelli, M.; Descouts, P.; Wells, T. N., Influence of surface and protein modification on immunoglobulin G adsorption observed by scanning force microscopy. *Biophysical journal* 1994, 67 (3), 1316-1323.
40. Chen, Y.; Cai, J.; Xu, Q.; Chen, Z. W., Atomic force bio-analytics of polymerization and aggregation of phycoerythrin-conjugated immunoglobulin G molecules. *Molecular immunology* 2004, 41 (12), 1247-1252.
41. Silverton, E. W.; Navia, M. A.; Davies, D. R., Three-dimensional structure of an intact human immunoglobulin. *Proceedings of the National Academy of Sciences* 1977, 74 (11), 5140-5144.
42. Aslan, K.; Lakowicz, J. R.; Szmacinski, H.; Geddes, C. D., Metal-enhanced fluorescence solution-based sensing platform. *Journal of fluorescence* 2004, 14 (6), 677-679.
43. Zhang, Y.; Dragan, A.; Geddes, C. D., Wavelength dependence of metal-enhanced fluorescence. *The Journal of Physical Chemistry C* 2009, 113 (28), 12095-12100.
44. Pompa, P. P.; Martiradonna, L.; Della Torre, A.; Della Sala, F.; Manna, L.; De Vittorio, M.; Calabi, F.; Cingolani, R.; Rinaldi, R., Metal-enhanced fluorescence of colloidal nanocrystals with nanoscale control. *Nature nanotechnology* 2006, 1 (2), 126.

We claim:

1. A chip comprising a dielectric substrate and discontinuous and disordered metallic nanostructures of flat island shapes thereon, and further comprising a thin-film stabilizing overlayer deposited on the dielectric substrate and discontinuous and disordered metallic nanostructures of flat island shapes, wherein the discontinuous and disordered metallic nanostructures of flat island shapes cover between 20-40% of the dielectric substrate, have an area density of between 5-600/$\mu m^2$, and have an area between 50-250,000 $nm^2$;
    wherein the thin-film stabilizing overlayer increases fluorescence enhancement of the chip; and
    wherein the discontinuous and disordered metallic nanostructures of flat island shapes are prepared by rapid thermal annealing.

2. The chip of claim 1, wherein the discontinuous and disordered metallic nanostructures of flat island shapes thereon are characterized in shape as hemi-spherical nanostructures, ellipsoidal nanostrucutures, peanut-shaped nanostructure, worm-like nanostructure, lace-like nanostructures, or any combination thereof.

3. A chip comprising a dielectric substrate and discontinuous and disordered metallic nanostructures of flat island shapes thereon, and further comprising a thin-film stabilizing overlayer deposited on the dielectric substrate and discontinuous and disordered metallic nanostructures of flat island shapes, wherein the discontinuous and disordered metallic nanostructures of flat island shapes cover between 20-40% of the dielectric substrate, have an area density of between 5-600/$\mu m^2$; have an average height between 10-60 nm, and have an area between 50-250,000 $nm^2$;
    wherein the thin-film stabilizing overlayer increases fluorescence enhancement of the chip; and
    wherein the discontinuous and disordered metallic nanostructures of flat island shapes are prepared by rapid thermal annealing.

4. The chip of claim 1, wherein the discontinuous and disordered metallic nanostructures of flat island shapes are formed of silver.

5. The chip of claim 1, wherein the thin-film stabilizing overlayer is between 2-15 nm thick.

6. A chip comprising a dielectric substrate and discontinuous and disordered metallic nanostructures of flat island shapes thereon and a thin-film stabilizing overlayer deposited on the dielectric substrate and discontinuous and the disordered metallic nanostructures of flat island shapes, wherein the stabilizing overlayer is a metal oxide or a polymer;
    wherein the thin-film stabilizing overlayer increases fluorescence enhancement of the chip; and
    wherein the discontinuous and disordered metallic nanostructures of flat island shapes are prepared by rapid thermal annealing.

7. The chip of claim 1, wherein the dielectric substrate is a glass substrate or a piezoelectric substrate.

8. The chip of claim 6, wherein the chip has an enhancement factor between 1.1-20.0 as compared to the dielectric substrate without the discontinuous and disordered metallic nanostructures of flat island shapes thereon.

9. A metallic nanostructure biosensor comprising the chip according to claim 1 and further comprising a target binding protein immobilized onto chip.

10. The metallic nanostructure biosensor of claim 9 further comprising a thin-film stabilizing overlayer, wherein the target binding protein immobilized onto the thin-film stabilizing overlayer.

11. The biosensor of claim 9, wherein the target binding protein is a fragment crystallisable (Fc) binding protein or a lectin.

12. The biosensor of claim 9 further comprising a target probe.

13. The biosensor of claim 12, wherein the target probe is a fluorescently labeled anti-antibody.

14. A method of fabricating a chip according to claim 1, the method comprising: depositing a thin metallic film on a dielectric substrate; and applying rapid thermal annealing to the metallic film to produce the discontinuous and disordered metallic nanostructures of flat island shapes.

15. The method of claim 14, wherein the metallic film is less than 25 nm thick.

16. The method of claim 14, wherein the rapid thermal annealing occurs at a temperature lower than a melting point of the metallic film.

17. The method of claim 14, wherein the rapid thermal annealing comprises heating the thin metallic film and the dielectric substrate up to an annealing temperate at an annealing rate, holding the thin metallic film and the dielectric substrate at the annealing temperature of an annealing time, and cooling the thin metallic film and the dielectric substrate to room temperature at a cooling rate.

18. The method of claim 14, wherein the metallic film is formed of silver.

19. The method of claim 14, further comprising coating the discontinuous and disordered metallic nanostructures of flat island shape with a thin stabilizing overlayer film, wherein shapes of the metallic nanostructures are retained after coating with the stabilizing overlayer.

20. The method of claim 19, wherein the stabilizing overlayer is between 2-15 nm thick.

21. A method for forming a metallic nanostructure biosensor, the method comprising immobilizing a target binding protein onto the chip according to claim 1.

22. The method of claim 21, wherein the chip further comprises a thin-film stabilizing overlayer deposited on the dielectric substrate and discontinuous and the disordered metallic nanostructures of flat island shapes and wherein the target binding protein is immobilized onto the stabilizing overlayer.

23. A method for detecting of a biomolecular target in a sample, the method comprising contacting the metallic nanostructure biosensor according to claim 9 with the sample and a target probe, irradiating the metallic nanoscruture biosensor, and detecting a signal, wherein the biomolecular target has binding affinity with the immobilized binding protein and the target probe.

24. The method of claim 23, wherein the biomolecular target is an antibody or a chitin.

25. The chip of claim 1, wherein the discontinuous and disordered metallic nanostructures of flat island shapes comprise nanoparticles; and wherein about 39% of the nanoparticles from the nanostructures having a 5 nm film thickness have areas in the range of 250-450 $nm^2$, or about 47% of the nanoparticles from the nanostructures having a 15 nm film thickness have areas in the range of 0.025-0.045 $\mu m^2$.

* * * * *